United States Patent [19]

Baserga et al.

[11] Patent Number: 6,084,085
[45] Date of Patent: Jul. 4, 2000

[54] INDUCING RESISTANCE TO TUMOR GROWTH WITH SOLUBLE IGF-1 RECEPTOR

[75] Inventors: Renato Baserga, Ardmore; Mariana Resnicoff, Philadelphia; Consuelo D'Ambrosio, Philadelphia; Andre Ferber, Philadelphia, all of Pa.

[73] Assignee: Thomas Jefferson University, Philadelphia, Pa.

[21] Appl. No.: 08/746,559

[22] Filed: Nov. 13, 1996

Related U.S. Application Data

[60] Provisional application No. 60/006,699, Nov. 14, 1995.

[51] Int. Cl.[7] .......................... A61K 38/00; C12N 15/85
[52] U.S. Cl. ................... 536/23.5; 435/325; 435/69.1; 536/23.1; 530/350; 514/12
[58] Field of Search ........................... 536/23.1; 514/44; 435/325; 530/350

[56] References Cited

U.S. PATENT DOCUMENTS

| | | | |
|---|---|---|---|
| 4,736,866 | 4/1988 | Leder et al. ................................ | 800/1 |
| 4,873,191 | 10/1989 | Wagner et al. ....................... | 435/172.3 |
| 5,139,941 | 8/1992 | Muzyczka et al. .................... | 435/172.3 |
| 5,173,414 | 12/1992 | Lebkowski et al. .................. | 435/172.3 |
| 5,227,466 | 7/1993 | DeMeyts ................................. | 530/305 |
| 5,252,479 | 10/1993 | Srivastava ............................ | 435/235.1 |
| 5,262,308 | 11/1993 | Baserga .................................. | 435/69.1 |
| 5,354,674 | 10/1994 | Hodgson ............................... | 435/172.3 |
| 5,354,678 | 10/1994 | Lebkowski et al. .................. | 435/172.3 |
| 5,399,346 | 3/1995 | Anderson et al. .................... | 424/93.21 |
| 5,460,831 | 10/1995 | Kossovsky et al. ..................... | 424/493 |

FOREIGN PATENT DOCUMENTS

| | | |
|---|---|---|
| 9117253 | 10/1991 | WIPO . |
| WO 91/17252 | 11/1991 | WIPO . |
| WO 94/22486 | 10/1994 | WIPO . |

OTHER PUBLICATIONS

Abraham, et al., "Survival and Development of larval *Onchocerca Volvulus* in Diffusion Chambers Implanted in Primate and Rodent Hosts", *J. Parasitol.*, 1993, 79, 571–582.

Arteaga, C.L., "Interference of the IGF system as a strategy to inhibit breast cancer growth", *Breast Canc. Res. Treatm.*, 1992, 22, 101–106.

Baker, J., et al., "Role of Insulin–like Growth Ffactors in Embryonic and Postnatal Growth", *Cell,* 1993, 75, 73–82.

Barry, M., et al., "Activation of Programmed Cell Death (Apoptosis) by Cisplatin, Other Anticancer Drugs, Toxins and Hyperthermia", *Biochem. Pharmacol.,* 1990, 40, 2353–2362.

Baserga, R. And Rubin, R., "Cell Cycle and Growth Control", *Crit. Rev. in Eukaryot. Gene Exp.*, 1993, 3, 47–61.

Baserga, R., "Controlling IGF–receptor function: a possible strategy for tumor therapy", *Trends in Biotech.*, 1996, 14, 150–152.

Baserga, R., "Oncogenes and the Strategy of Growth Factors", *Cell,* 1994, 79, 927–930.

Bursch, W., et al., "Determination of the length of the histological stagesof apoptosis in normal liver and in altered hepatic foci of rats", *Carcinogenesis,* 1990, 11, 847–853.

Buttyan, R., et al., "Induction of the TRPM–2 Gene in Cells Undergoing Programmed Death", *Mol. Cell. Biol.,* 1989, 9, 3473–3481.

Christofori, G. And Hanaham, P.N.& D., "A second signal supplied by insulin–like growth factor II in oncogene–induced tumorigenesis", *Nature,* 1994, 369, 414–418.

Coppola, D., et al., "A Functional Insulin–Like Growth Factor I Receptor Is Required for theMitogenic and Transforming Activities of the Epidermal Growth Factor Receptor", *Mol. Cell. Biol.,* 1994, 14, 4588–4595.

DeAngelis, T., et al., "Insulin–Like Growth Factor I Receptor is Required for the Mitogenic and Transforming Activities of the Platelet–Derived Growth Factor Receptor", *J. Cell. Physiol.,* 1995, 164, 214–221.

DiAmbrosio, C., et al., "A Soluble Insulin–like Growth Factor I Receptor That Induces Apoptosis of Tumor Cells in Vivo and Inhibits Tumorigenesis", *Cancer Res.,* 1996, 56, 4013–4020.

Goldring, M.B. and S., "Cytokines and Cell Growth Control", *Crit. Rev. Eukaryot. Gene Exp.,* 1991, 1, 301–326.

Kalebic, T., et al., "In Vivo Treatment with Antibody against IGF–1 Receptor Suppresses Growth of Human Rhabdomyosarcoma and Down–Regulates $p34^{cdc2}$", *Cancer Res.,* 1994, 54, 5531–5534.

Kaleko, M., et al., "Overexpression of the Human Insulin-like Growth Factor I Receptor Promotes Ligand–Dependent Neoplastic Transformation", *Mol. Cell. Biol.,* 1990, 10, 464–473.

Kauffman, S., "Induction of Endonucleolytic DNA Cleavage in Human Acute Myelogenous Leukemia Cells by Etoposide, Camptothecin, and other Cytotoxic Anticancer Drugs: A Cautiionary Note[1]", *Cancer Res.,* 1989, 49, 5870–5878.

Lange, A.M., et al., "IL–4–and IL–5–Dependent Protective Immunity to *Onchocerca volvulus* Infective Larvae in BALB/BYj mice[1]", *Immunol.,* 1994, 153, 205–211.

Lanza, R.P., et al., "Xenogeneic Humoral Responses to Islets Transplanted in Biohybrid Diffusion Chambers", *Transplantation,* 1994, 57, 1371–1375.

Li, S., et al., "Mitogenicity and Transforming Activity of the Insulin–like Growth Factor–I Receptor with Mutations in the Tyrosine Kinase Domain", *J. Biol. Chem.,* 1994, 269, 32558–32564.

(List continued on next page.)

*Primary Examiner*—Paula K. Hutzell
*Assistant Examiner*—Minh-Tam Davis
*Attorney, Agent, or Firm*—Woodcock Washburn Kurtz Mackiewic & Norris, LLP

[57] ABSTRACT

Individuals having tumors are treated with pharmaceutical compositions comprising expression vectors, preferably adenovirus or retroviruses, comprising nucleic acid molecules encoding soluble IGF-1R. Such vectors express soluble IGF-1R in tumor cells resulting in reversal of the transformed phenotype, induction of apoptosis, and inhibition of tumorigenesis.

12 Claims, 10 Drawing Sheets

OTHER PUBLICATIONS

Liu, J., et al., "Mice Carrying Null Mutations of the Genes Encoding Insulin–like Growth Factor 1 (lgf–1) and Type 1 IGF Receptor (lgf1r)", *Cell*, 1993, 75, 59–72.

Long, L., et al., "Loss of the Metastatic Phenotype in Murine Carcinoma Cells Expressing an Antisense RNA to the Insulin–like Growth Factor Receptor[1]", *Cancer Res.*, 1995, 55, 1006–1009.

McCubrey, J.A., et al., "Growth–Promoting Effects of Insulin–Like Growth Factor–1(IGF–1) on Hematopoietic Cells: Overexpression of Introduced IGF–1 Receptor Abrogates Interleukin–3 Dependency of Murine Factor–Dependent Cells by a Ligand–Dependent Mechanism", *Blood*, 1991, 78, 921–929.

Miura, M., et al., "Effect of a Mutation at Tyrosine 950 of the Insulin–like Growth Factor Receptor on the Growth and Transformation of Cells[1]", *Cancer Res.*, 1995, 55, 663–667.

Pietrzkowski, Z., et al., "Roles of Insulinlike Growth Factor 1 (IGF–1) and the IGF–1 Receptor in Epidermal Growth Factor–Stimulated Growth of 3T3 Cells", *Mol. Cell Biol.*, 1992, 12, 3883–3889.

Pietrzykowski, Z., et al., "Constitutive Expression of Insulin–like Growth Factor 1 and Insulin–like Growth Factor 1 Rceptor Abrogates All Requirements for Exogenous Growth Factors[1]", *Cell Growth & Diff.*, 1992, 3, 199–205.

Preston, G.A., et al., "Regulation of Apoptosis by Low Serum in Cells of Different Stages of Neoplastic Progression: Enhanced Susceptibility after Loss of a Senescence Gene and Decreased Susceptibility after Loss of a Tumor Suppressor Gene", *Cancer Res.*, 1994, 54, 4214–4223.

Resnicoff, M., et al., "Rat Glioblastoma Cells Expressing an Antisense RNA to the Insulin–like Growth Factor–1 (IGF–1) Receptor Are Nontumorigenic and Induce Regression of Wild–Type Tumors[1]", *Cancer Res.*, 1994, 54, 2218–2222.

Resnicoff, M., et al., "The Insulin–like Growth Factor I Receptor Protects Tumor Cells from Apoptosis in Vivo[1]" *Cancer Res.*, 1995, 55, 2463–2469.

Resnicoff, M., et al., "Growth Inhibition of Human Melanoma Cells in Nude Mice by Antisense Strategies to the Type 1 Insulin–like Growth Factor Receptor[1]", *Cancer Res.*, 1994, 54, 4848–4850.

Resnicoff, M., et al., "Correlation between Apoptosis, Tumorigenesis, and Levels of Insulin–like Growth Factor I Receptors", *Cancer Res.*, 1995, 55, 3739–3741.

Rogler, C.E., et al., "Altered Body Composition and Increased Frequency of Diverse Malignancies in Insulin–Like Growth Factor II Transgenic Mice", *J. Biol. Chem.*, 1994, 269, 13779–13784.

Scher, C.D., et al., "Platelet–Derived Growth Factor and the Regulation of the Mammalian Fibroblast Cell Cycle", *Biochem. Biophys. Acta.*, 1979, 560, 217–241.

Sell, C., et al., "Insulin–like Growth Factor I (IGF–1) and the IGF–1 Receptor Prevent Etoposide–induced Apoptosis[1]", *Cancer Res.*, 1995, 55, 303–306.

Sell, C., et al., "Effect of a Null Mutation of the Insulin–Like Growth Factor I Receptor Gene on Growth and Transformation of Mouse Embryo Fibroflasts", *Mol. Cell. Biol.*, 1994, 14, 3604–3612.

Sell, C., et al., "Simian virus 40 large tumor antigen is unable to transform mouse embryonic fibroblasts lacking type 1 insulin–like growth factor receptor", *Proc. Natl. Acad. USA*, 1993, 90, 11217–11221.

Shapiro, D.N., et al, "Antisense–mediated Reduction in Insulin–like Growth Factor–1 Receptor Expression Suppresses the Malignant Phenotype of a Human Alveolar Rhabdomyosarcoma", *J. Clin. Invest.*, 1994, 94, 1235–1242.

Stiles, C.D., et al., "Dual control of cell growth by somatomedins and platelet–derived growth factor", *Proc. Natl. Acad. Sci. USA*, 1979, 76, 1279–1283.

Surmacz E., et al., "Dissociation of Mitogenesis and Transforming Activity by C–Terminal Truncation of the Insulin–like Growth Factor–1 Receptor", *Exp. Cell. Res.*, 1995, 218, 370–380.

Trojan, J., et al., "Treatment and Prevention of Rat Glioblastoma by Immunogenic C6 Cells Expressing Antisense Insulin–Like Growth Factor 1 RNA", *Science*, 1993, 259, 94–97.

Trojan, J., et al., "Loss of tumorogenicity of rat glioblastoma directed by episome–based antisense cDNA transcription of insulin–like growth factor I", *Proc. Natl. Acad. Sci. USA*, 1992, 89, 4874–4878.

Campbell, P.G., et al., "Insulin–like growth factor binding protein (IGFBP) inhibits IGF action on human osteosarcoma cells", *J. Cell. Physiol.*, 1991, 149, 293–300.

Ullrich, A. And Schlessinger, J., "Signal Transduction by Receptors with Tyrosine Kinase Activity", *Cell*, 1990, 61, 203–212.

Zhou–Li, F., et al., "Association of Insulin Receptor Substrate 1 with Simian Virus 40 Large T Antigen", *Mol. Cell Biol.*, 1995, 15, 4232–4239.

Prager, D., et al., "Dominant negative inhibition of tumorigenesis in vivo by human insulin growth factor I receptor mutant", *Proc. Natl. Acad. Sci. USA*, 1994, 91, 2181–2185.

Ullrich, A. et al. 1986. Embo J. 5:2503–2512.

FIG. 1A

```
     CysGlnLysMetCys ProSerThrCysGlyLysArgAlaCysThrGluAsnAsnGluCysHisProGluCys
     TGCCAGAAAATGTGCCCCAAGCACGTGTGGGAAGCGGGGGCTGCACCGAGAACAATGAGTGCCACCCCGAGTGC                          750
        190                              200
     LeuGlySerCysSerAlaProAspAsnAspThrAlaCysValAlaCysArgHisTyrTyrAlaGlyValCys
     CTGGGCAGCTGCAGCGCCCTGACAACGACACGGCCTGTGTAGCTGCCGCCACTACTACGCGGTGTCTGT                              900
              210                              220                              230
     ValProAlaCysProProAsnThrTyrArgPheGluGlyGlyPheValIleHisAspSerGlyValAspArgAspPheCysValAspArgAspPheCysAlaAsnIle
     GTGCCTGCCTGCCCGCCCAACACCTACAGGTTTGAGGGCTGCCGCCTGTGTGATCCACGAGGGCGTGACTTCTGCGCCAACATC                    900
                 240                             250
     LeuSerAlaGluSerSerAspSerGlyPheValIleHisAspSerGlyGluAspArgGluCysMetGlnGluCysProSerGly
     CTCAGCGCCGAGAGCAGCGACTCCGAGGGGTTTGTGATCCACGACGCGGGCGAGTGCATGCAGGAGTGCCCCTCGGGC        280           1050
                      260                             270
     PheIleArgAsnGlySerGlnSerMetTyrCysIleProCysGluGlyProCysProLysValCysGluGluGlu
     TTCATCCGCAACGGCAGCCAGAGCATGTACTGCATCCCTTGTGAAGGTCCTTGCCCGAAGGTCTGTGAGGAAGAA                          1050
                    290                              300
     LysLysThrLysAspSerValThrSerAlaGlnMetLeuGlnGlyCysThrIlePheLysGlyAsnLeu
     AAGAAAACAAAGGACAGTGTTACTTCTGTTACCTTGTTACCTTGCTCCAAGGATGCCACCATCTTCAAGGGCAATTG                       1200
                           320                             330
     LeuIleAsnIleArgArgGlyAsnAsnIleAlaSerGluLeuGluAsnPheMetGlyIleLeuGluArgLeuLeuValThr
     CTCATTAACATCCGACGGGGAATAACATTGCTTCAGAGCTTGGAGAACTTCATGGGGCTCATCGAGGTGGTGACG                         1200
                 340                              350
     GlyTyrValLysIleArgHisSerLeuLeuValSerLeuAsnLeuArgLeuIleGly
     GGCTACGTGAAGATCCGCCATTCTCATGGCCTTGGTCCTTGCTAAAAACCTTGCCTCTCATCCTAGGA                               1350
                       360                             370                             380
     GluGluGlnLeuGluGlyAsnTyrSerPheTyrValLeuAspAsnGlnLeuTrpAspAsp
     GAGGAGCAGCTAGAAGGGAATTACTCCTTCTACGTCCTTGACAACCAGAACTTGCAGGACTGGGAC                                 1350
                             390                            400
```

FIG. 1B

```
                410
HisArgAsnLeuThrIleLysAlaGlyLysMetTyrPheAlaProLysLeuCysValSerGluIleTyr    430
CACCGCAACCTGACCATCAAAGCAGGGAAAATGTACTTTGCTTTCAATCCCAAATTATGTTTCGAAATTTAC

440
ArgMetGluValThrGlyThrLysGlyArgGlnSerLysGlyAspIleAsnThrArgAsnAsnGlyGluArg    1500
CGCATGGAGGAAGTGACGGGCACTAAAGGGCGCCAAAGCAAAGGGGACATAAACACCAGGAACAACGGGGAGAGA 460                          470                          480
AlaSerCysGluSerAspValLeuHisPheThrSerThrThrSerLysAsnArgIleIleIleThrTrpHis
GCCTCCTGTGAAAGTGACGTCCTGCATTTCACCTCCACCACGTCGAAGAATCGCATCATCATAACCTGGCAC 490                                       500
ArgTyrArgProProAspTyrArgAspLeuIleSerPheThrValTyrTyrLysGluAlaProPheLysAsnVal
CGGTACCGCCCCCCTGACTACAGGGATCTCATCAGCTTCACCGTTTACTACAAGGAAGCACCCTTTAAGAATGTC    1650

510                          520                          530
ThrGluTyrAspGlyGlnAspAlaCysGlySerAsnSerTrpAsnMetValAspValAspLeuProAsnLys
ACAGAGTACGATGGGCAGGATGCCTGCGGCTCCAACAGCTGGAACATGGTGGACGTGGACCTCCCCAACAAG 540                          550
AspValGluProGlyIleLeuLeuHisGlyLeuLysProTrpThrGlnTyrAlaValTyrValAlaValThr
GACGTGGAGCCCGGCATCTTACTACACGGCCTGAAGCCCTGGACTCAGTATGCAGTGTACGTGGCCGTGACC 560                          570                          580
LeuThrMetValGluAsnAspHisIleArgGlyAlaAlaLysSerGluIleLeuTyrIleArgThrAsnAlaSerVal
CTCACCATGGTGGAGAACGACCATATCCGTGGGGCCGCCAAGAGTGAGATCTTGTACATTCGAACCAATGCTTCAGTT 590                          600
ProSerIleProLeuAspValLeuSerAlaSerAsnSerSerSerGlnLeuIleValLysTrpAsnProProSer
CCCTTCCATTCCCTTGGACGTTCTTTCAGCATCGAACTCCTCTTCTCAGTTAATCGTGAAGTGGAACCCCCTCT    1950

610                          620                          630
LeuProAsnGlyAsnLeuSerTyrTyrIleValArgGlnProGlnArgTrpGlnProGlnAspGlyTyrLeuArgHis
CTGCCCAACGGCAACCTGAGTTACTACATTGTGCGTCAGCCTCAGCGGTGGCAGCCTCAGGACGGCTACCTTTACCGGCAC
```

```
                                                                                2850
ArgLysTyrGlyGlyAlaLysLeuAsnArgLeuAsnAlaArgIleGlnAlaThrSerLeu
AGGAAGTATGGAGGGGCCAAGCTAAACCGGCTAAACCCGGATTCAGGCCACATCTCTC
                860              870              880

SerGlyAsnGlySerTrpThrAspProValPhePheTyrValGlnAlaLysThrGlyTyrGluAsnPheIleHis
TCTGGGAATGGGTCGTGGACAGATCCTGTTCTTCTTATGTCCAGGCCAAAACAGGATATGAAAACTTCATCCAT
                890              900                              930
LeuIleIleAlaLeuProValAlaValLeuLeuIleValGlyGlyLeuValIleMetLeuTyrValPheHisArg
CTGATCATCGCTCTGCCCGTCGTCCTGCTCATCGTGGGAGGGTTGGTGATTATGCTGTACGTCTTCCATAGA
                910              920              930
                                                                                3000
LysArgAsnAsnSerArgArgLeuGlyAsnGlyValLeuTyrAlaSerValAsnProGluTyrPheSerAlaAlaAsp
AAGAGAAATAACAGCAGGCTGGGGAATGGAGTGCTGTATGCCTCTGTGAACCCGGAGTACTTCAGCGCTGCTGAT
                940              950

ValTyrValProAspGluTrpGluValAlaAlaArgGluLysIleThrMetSerArgGluLeuGlyGlnGlySerPhe
GTGTACGTTCCTGATGAGTGGGAGGTGGCTGCTCGGGAGAAGATCACCATGAGCCGGGAACTTGGGCAGGGGTCGTTT
                960              970                              980
                                                                                3150
GlyMetValTyrGluGlyValAlaAlaLysGlyValValValLysAspGluProGluThrArgValAlaIleLysThrVal
GGGATGGTCTATGAAGGAGTTGCCGCAAAGGGTGTGGTAGTAAAGGATGAACCTGAAACCAGAGTGGCCATTAAAACAGTG
                990              1000

AsnGluAlaAlaSerMetArgGluArgIleGluPheLeuAsnGluAlaSerValMetLysGluPheAsnCysHis
AACGAGGCCGCAAGCATGCGTGAGAGGATTGAGTTTCTCAACGAAGCTTCTGTGATGAAGGAGTTCAATTGTCAC
                1010              1020              1030

HisValAlaArgLeuLeuGlyValValSerGlnGlyGlnProThrLeuValIleMetGluLeuMetThrArgGly
CATGTGGCGAGGCTGCTTGGTGTGGTGTCCCAAGGCCAACACTGGTCATCATGGAACTGATGACACGGGGC
                1040              1050
                                                                                3300
AspLeuLysSerTyrLeuArgSerLeuArgProGluMetGluAsnAsnProValLeuAlaProProSerLeuSer
GATCTCAAAAGTTATCTCCGGTCTCTGAGGCCAGAAATGGAGAATAATCCAGTCCTAGCACCTCCAAGCCTGAGC
                1060              1070              1080
```

FIG. 1E

```
                                              1100
LysMetIleGlnMetAlaGlyGluIleAlaAspGlyMetAlaTyrLeuAsnAlaAsnLysPheValHisArgAsp
AAGATGATTCAGATGGCCGGAGAGATTGCAGACGGCATGGCATACCTCAACGCCAATAAGTTCGTCCACAGAGAC  3450
                                     1130
         1110             LeuAlaAlaArgAsnCysMetValAlaGluAspPheThrValLysIleGlyAspPheGlyMetThrArgAspIle
CTTGCTGCCAGGAATTGCATGGTAGCCGAAGATTTCACAGTCAAAATCGGAGATTTTGGTATGACGCGAGATATC
                                              1150
TyrGluThrAspTyrTyrArgLysGlyGlyLysGlyLeuLeuProValArgTrpMetSerProGluSerLeuLys
TATGAGACAGACTATTACCGGAAAGGAGGGAAAGGGCTGCTGCCGGTGCGCTGGATGTCTCCTGAGTCCCTCAAG  3600
                                              1180
AspGlyValPheThrThrTyrSerAspValTrpSerPheGlyValValLeuTrpGluIleAlaThrLeuAlaGlu
GATGGAGTCTTCACCACTTACTCGGACGTCTTGGTCTTTGGGGTTGTCCTCTGGGAGATCGCCACACTGGCCGAG
                                              1200
GlnProTyrGlnGlyLeuSerAsnGluGlnValLeuArgPheValMetGluGlyGlyLeuLeuAspLysProAsp
CAGCCCTACCAGGGCCTTGTCCAACGAGCAAGTCCTTCGCTTCGTCATGGAAGGGGGCCTTCTGGACAAGCCAGAC  3750
                                              1230
AsnCysProAspMetLeuPheGluLeuMetArgMetCysTrpGlnTyrAsnProLysMetArgProSerPheLeu
AACTGTCCTGACATGCTGTTTGAACTGATGCGCATGTGCTGGCAGTATAACCCCAAGATGAGGCCTTCCTTCCTG
                                              1250
GluIleIleSerSerIleLysGluGluMetGluProGlyPheArgGluValSerPheTyrTyrSerGluGluAsn
GAGATCATCAGCAGCATCAAAGAGGAGATGGAGCCTGGACTTCCGGGAGGTCTCCTTCTACTACAGCGAGGAGAAC  3900
                                              1280
LysLeuProGluProGluGluLeuAspLeuGluProGluAsnMetGluSerValProLeuAspProSerAlaSer
AAGCTGCCCGAGCCCGAGGAGCTGGACCTGGAGCCAGAGAACATGGAGAGCGTCCCCCTGGACCCCTCGGCCTCC
                                              1300
SerSerLeuProAspArgHisSerGlyHisLysAlaGluAsnGlyProGlyValLeuVal
TCGTCCTCCCTGCCCGACAGGCACTCAGGACACAAGGCCGAGAACGGCCCCGGGGTGCTGGTC  4050
```

```
                   1310                            1320
     LeuArgAlaSerPheAspGluArgGlnArgGluArgGlyGlyArgLysAsnGluArgAlaLeuPro
                                                                              1330
     CTCCGCGGCCAGCTTCGACGAGAGAGACAGCCTTACGCCCACATGAAGCCCAAGAACGAGCGGGCCTTGCCG

LeuProGlnSerSerThrCysEnd
     CTGCCCCAGTCTTCGACCTGCTGATCCTGAATCTGTGCAAACAGTAAGCGTGTGCGCACGCGCAGCGG     4200
     GGTGGGGGGGAGAGAGAGTTTTAACAATCCATTCACAAGCCTCCTGTACCTCAGTGGATCTTCAGTTCTGCCCT  4350
     TGCTGCCCGCGGGAGACAGCTTCTCTGCAGTAAAACACATTTGGGATGTTCCTTTTTCAATATGCAAGCAGCTT
     TTTATTCCCTGCCCAAACCCTTAACTGACACATGGGCCTTTAAGAACCCTTAATGACAACACTTAATAGCAACAGAGC  4500
     ACTTGAGAACCAGTCTCCTCACTCTGTCCCTGTCCCTTTCTCCCTTTCTCTCCTCTCTGCTTCATAAC
     GGAAAAATAATTGCCACAGTGGGAAGCCCCTGGGTCATTACAAAAAACACGTGGCTGTCCCGTGGCCCC       4650
     ATCCAACCACTGTACACACCCGCTGACACCGTGGGACACCGCCTGACACCCGCCTGTTCATCCAAGGCTGTTACCATTTTAACGC
     TTATCTTTCACCTTTCTAGGGACATGAAACTTTCTCGAACTTTCTCCCTCATCGGCCCGGCTGATTCCTCGTGTCCGGAGGCATGGG  4800
     TGCCTAATTTTGCCAAAATCCTGAACTTTCTCCCTCATCGGCCCGGCTGGCGACACTCCGTCCATCCGACTGCCCCTGTGT      4950
     TGAGCATGGCAGCTGGTTGCTCCATTGAGAGACACGCTGGCGACACGCCGACACTCCGTCCATCCGACTGCCCCTGTGT
     GCTGCTCAAGGCCACAGGCACACAGGTCTCATTGCTTCTGACTAGATTATTATTTGGGGAACTGGACACAATAG
     GTCTTTCTCTCAGTGAAGGTGGGGAGAAGCTGAACCGGC                                  4989
```

Diffusion Chamber

SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
       (A) LENGTH: 4989 base pairs
       (B) TYPE: nucleic acid
       (C) STRANDEDNESS: double
       (D) TOPOLOGY: linear (xi) SEQUENCE DESCRIPTION: SEQ ID NO: 1:

```
TTTTTTTTTT TTTTGAGAAA GGGAATTTCA TCCCAAATAA AAGGA ATG AAG TCT            54
                                                  Met Lys Ser
                                                    1

GGC TCC GGA GGA GGG TCC CCG ACC TCG CTG TGG GGG CTC CTG TTT              99
Gly Ser Gly Gly Gly Ser Pro Thr Ser Leu Trp Gly Leu Leu Phe
      5                   10                  15

CTC TCC GCC GCG CTC TCG CTC TGG CCG ACG AGT GGA GAA ATC TGC             144
Leu Ser Ala Ala Leu Ser Leu Trp Pro Thr Ser Gly Glu Ile Cys
         20                  25                  30

GGG CCA GGC ATC GAC ATC CGC AAC GAC TAT CAG CAG CTG AAG CGC             189
Gly Pro Gly Ile Asp Ile Arg Asn Asp Tyr Gln Gln Leu Lys Arg
         35                  40                  45

CTG GAG AAC TGC ACG GTG ATC GAG GGC TAC CTC CAC ATC CTG CTC             234
Leu Glu Asn Cys Thr Val Ile Glu Gly Tyr Leu His Ile Leu Leu
         50                  55                  60

ATC TCC AAG GCC GAG GAC TAC CGC AGC TAC CGC TTC CCC AAG CTC             279
Ile Ser Lys Ala Glu Asp Tyr Arg Ser Tyr Arg Phe Pro Lys Leu
         65                  70                  75

ACG GTC ATT ACC GAG TAC TTG CTG CTG TTC CGA GTG GCT GGC CTC             324
Thr Val Ile Thr Glu Tyr Leu Leu Leu Phe Arg Val Ala Gly Leu
         80                  85                  90

GAG AGC CTC GGA GAC CTC TTC CCC AAC CTC ACG GTC ATC CGC GGC             369
Glu Ser Leu Gly Asp Leu Phe Pro Asn Leu Thr Val Ile Arg Gly
         95                 100                 105

TGG AAA CTC TTC TAC AAC TAC GCC CTG GTC ATC TTC GAG ATG ACC             414
Trp Lys Leu Phe Tyr Asn Tyr Ala Leu Val Ile Phe Glu Met Thr
        110                 115                 120

AAT CTC AAG GAT ATT GGG CTT TAC AAC CTG AGG AAC ATT ACT CGG             459
Asn Leu Lys Asp Ile Gly Leu Tyr Asn Leu Arg Asn Ile Thr Arg
        125                 130                 135

GGG GCC ATC AGG ATT GAG AAA AAT GCT GAC CTC TGT TAC CTC TCC             504
Gly Ala Ile Arg Ile Glu Lys Asn Ala Asp Leu Cys Tyr Leu Ser
        140                 145                 150

ACT GTG GAC TGG TCC CTG ATC CTG GAT GCG GTG TCC AAT AAC TAC             549
Thr Val Asp Trp Ser Leu Ile Leu Asp Ala Val Ser Asn Asn Tyr
        155                 160                 165

ATT GTG GGG AAT AAG CCC CCA AAG GAA TGT GGG GAC CTG TGT CCA             594
Ile Val Gly Asn Lys Pro Pro Lys Glu Cys Gly Asp Leu Cys Pro
        170                 175                 180

GGG ACC ATG GAG GAG AAG CCG ATG TGT GAG AAG ACC ACC ATC AAC             639
Gly Thr Met Glu Glu Lys Pro Met Cys Glu Lys Thr Thr Ile Asn
        185                 190                 195

AAT GAG TAC AAC TAC CGC TGC TGG ACC ACA AAC CGC TGC CAG AAA             684
Asn Glu Tyr Asn Tyr Arg Cys Trp Thr Thr Asn Arg Cys Gln Lys
        200                 205                 210

ATG TGC CCA AGC ACG TGT GGG AAG CGG GCG TGC ACC GAG AAC AAT             729
```

```
Met Cys Pro Ser Thr Cys Gly Lys Arg Ala Cys Thr Glu Asn Asn
215                 220                 225

GAG TGC TGC CAC CCC GAG TGC CTG GGC AGC TGC AGC GCG CCT GAC        774
Glu Cys Cys His Pro Glu Cys Leu Gly Ser Cys Ser Ala Pro Asp
230                 235                 240

AAC GAC ACG GCC TGT GTA GCT TGC CGC CAC TAC TAC TAT GCC GGT        819
Asn Asp Thr Ala Cys Val Ala Cys Arg His Tyr Tyr Tyr Ala Gly
245                 250                 255

GTC TGT GTG CCT GCC TGC CCG CCC AAC ACC TAC AGG TTT GAG GGC        864
Val Cys Val Pro Ala Cys Pro Pro Asn Thr Tyr Arg Phe Glu Gly
260                 265                 270

TGG CGC TGT GTG GAC CGT GAC TTC TGC GCC AAC ATC CTC AGC GCC        909
Trp Arg Cys Val Asp Arg Asp Phe Cys Ala Asn Ile Leu Ser Ala
275                 280                 285

GAG AGC AGC GAC TCC GAG GGG TTT GTG ATC CAC GAC GGC GAG TGC        954
Glu Ser Ser Asp Ser Glu Gly Phe Val Ile His Asp Gly Glu Cys
290                 295                 300

ATG CAG GAG TGC CCC TCG GGC TTC ATC CGC AAC GGC AGC CAG AGC        999
Met Gln Glu Cys Pro Ser Gly Phe Ile Arg Asn Gly Ser Gln Ser
305                 310                 315

ATG TAC TGC ATC CCT TGT GAA GGT CCT TGC CCG AAG GTC TGT GAG       1044
Met Tyr Cys Ile Pro Cys Glu Gly Pro Cys Pro Lys Val Cys Glu
320                 325                 330

GAA GAA AAG AAA ACA AAG ACC ATT GAT TCT GTT ACT TCT GCT CAG       1089
Glu Glu Lys Lys Thr Lys Thr Ile Asp Ser Val Thr Ser Ala Gln
335                 340                 345

ATG CTC CAA GGA TGC ACC ATC TTC AAG GGC AAT TTG CTC ATT AAC       1134
Met Leu Gln Gly Cys Thr Ile Phe Lys Gly Asn Leu Leu Ile Asn
350                 355                 360

ATC CGA CGG GGG AAT AAC ATT GCT TCA GAG CTG GAG AAC TTC ATG       1179
Ile Arg Arg Gly Asn Asn Ile Ala Ser Glu Leu Glu Asn Phe Met
365                 370                 375

GGG CTC ATC GAG GTG GTG ACG GGC TAC GTG AAG ATC CGC CAT TCT       1224
Gly Leu Ile Glu Val Val Thr Gly Tyr Val Lys Ile Arg His Ser
380                 385                 390

CAT GCC TTG GTC TCC TTG TCC TTC CTA AAA AAC CTT CGC CTC ATC       1269
His Ala Leu Val Ser Leu Ser Phe Leu Lys Asn Leu Arg Leu Ile
395                 400                 405

CTA GGA GAG GAG CAG CTA GAA GGG AAT TAC TCC TTC TAC GTC CTC       1314
Leu Gly Glu Glu Gln Leu Glu Gly Asn Tyr Ser Phe Tyr Val Leu
410                 415                 420

GAC AAC CAG AAC TTG CAG CAA CTG TGG GAC TGG GAC CAC CGC AAC       1359
Asp Asn Gln Asn Leu Gln Gln Leu Trp Asp Trp Asp His Arg Asn
425                 430                 435

CTG ACC ATC AAA GCA GGG AAA ATG TAC TTT GCT TTC AAT CCC AAA       1404
Leu Thr Ile Lys Ala Gly Lys Met Tyr Phe Ala Phe Asn Pro Lys
440                 445                 450

TTA TGT GTT TCC GAA ATT TAC CGC ATG GAG GAA GTG ACG GGG ACT       1449
Leu Cys Val Ser Glu Ile Tyr Arg Met Glu Glu Val Thr Gly Thr
455                 460                 465

AAA GGG CGC CAA AGC AAA GGG GAC ATA AAC ACC AGG AAC AAC GGG       1494
Lys Gly Arg Gln Ser Lys Gly Asp Ile Asn Thr Arg Asn Asn Gly
470                 475                 480

GAG AGA GCC TCC TGT GAA AGT GAC GTC CTG CAT TTC ACC TCC ACC       1539
Glu Arg Ala Ser Cys Glu Ser Asp Val Leu His Phe Thr Ser Thr
485                 490                 495

ACC ACG TCG AAG AAT CGC ATC ATC ATA ACC TGG CAC CGG TAC CGG       1584
Thr Thr Ser Lys Asn Arg Ile Ile Ile Thr Trp His Arg Tyr Arg
500                 505                 510
```

```
                                                         -continued

CCC CCT GAC TAC AGG GAT CTC ATC AGC TTC ACC GTT TAC TAC AAG        1629
Pro Pro Asp Tyr Arg Asp Leu Ile Ser Phe Thr Val Tyr Tyr Lys
515                 520                 525

GAA GCA CCC TTT AAG AAT GTC ACA GAG TAT GAT GGG CAG GAT GCC        1674
Glu Ala Pro Phe Lys Asn Val Thr Glu Tyr Asp Gly Gln Asp Ala
        530                 535                 540

TGC GGC TCC AAC AGC TGG AAC ATG GTG GAC GTG GAC CTC CCG CCC        1719
Cys Gly Ser Asn Ser Trp Asn Met Val Asp Val Asp Leu Pro Pro
545                 550                 555

AAC AAG GAC GTG GAG CCC GGC ATC TTA CTA CAT GGG CTG AAG CCC        1764
Asn Lys Asp Val Glu Pro Gly Ile Leu Leu His Gly Leu Lys Pro
        560                 565                 570

TGG ACT CAG TAC GCC GTT TAC GTC AAG GCT GTG ACC CTC ACC ATG        1809
Trp Thr Gln Tyr Ala Val Tyr Val Lys Ala Val Thr Leu Thr Met
575                 580                 585

GTG GAG AAC GAC CAT ATC CGT GGG GCC AAG AGT GAG ATC TTG TAC        1854
Val Glu Asn Asp His Ile Arg Gly Ala Lys Ser Glu Ile Leu Tyr
        590                 595                 600

ATT CGC ACC AAT GCT TCA GTT CCT TCC ATT CCC TTG GAC GTT CTT        1899
Ile Arg Thr Asn Ala Ser Val Pro Ser Ile Pro Leu Asp Val Leu
605                 610                 615

TCA GCA TCG AAC TCC TCT TCT CAG TTA ATC GTG AAG TGG AAC CCT        1944
Ser Ala Ser Asn Ser Ser Ser Gln Leu Ile Val Lys Trp Asn Pro
        620                 625                 630

CCC TCT CTG CCC AAC GGC AAC CTG AGT TAC TAC ATT GTG CGC TGG        1989
Pro Ser Leu Pro Asn Gly Asn Leu Ser Tyr Tyr Ile Val Arg Trp
635                 640                 645

CAG CGG CAG CCT CAG GAC GGC TAC CTT TAC CGG CAC AAT TAC TGC        2034
Gln Arg Gln Pro Gln Asp Gly Tyr Leu Tyr Arg His Asn Tyr Cys
        650                 655                 660

TCC AAA GAC AAA ATC CCC ATC AGG AAG TAT GCC GAC GGC ACC ATC        2079
Ser Lys Asp Lys Ile Pro Ile Arg Lys Tyr Ala Asp Gly Thr Ile
665                 670                 675

GAC ATT GAG GAG GTC ACA GAG AAC CCC AAG ACT GAG GTG TGT GGT        2124
Asp Ile Glu Glu Val Thr Glu Asn Pro Lys Thr Glu Val Cys Gly
        680                 685                 690

GGG GAG AAA GGG CCT TGC TGC GCC TGC CCC AAA ACT GAA GCC GAG        2169
Gly Glu Lys Gly Pro Cys Cys Ala Cys Pro Lys Thr Glu Ala Glu
695                 700                 705

AAG CAG GCC GAG AAG GAG GAG GCT GAA TAC CGC AAA GTC TTT GAG        2214
Lys Gln Ala Glu Lys Glu Glu Ala Glu Tyr Arg Lys Val Phe Glu
        710                 715                 720

AAT TTC CTG CAC AAC TCC ATC TTC GTG CCC AGA CCT GAA AGG AAG        2259
Asn Phe Leu His Asn Ser Ile Phe Val Pro Arg Pro Glu Arg Lys
725                 730                 735

CGG AGA GAT GTC ATG CAA GTG GCC AAC ACC ACC ATG TCC AGC CGA        2304
Arg Arg Asp Val Met Gln Val Ala Asn Thr Thr Met Ser Ser Arg
        740                 745                 750

AGC AGG AAC ACC ACG GCC GCA GAC ACC TAC AAC ATC ACC GAC CCG        2349
Ser Arg Asn Thr Thr Ala Ala Asp Thr Tyr Asn Ile Thr Asp Pro
755                 760                 765

GAA GAG CTG GAG ACA GAG TAC CCT TTC TTT GAG AGC AGA GTG GAT        2394
Glu Glu Leu Glu Thr Glu Tyr Pro Phe Phe Glu Ser Arg Val Asp
        770                 775                 780

AAC AAG GAG AGA ACT GTC ATT TCT AAC CTT CGG CCT TTC ACA TTG        2439
Asn Lys Glu Arg Thr Val Ile Ser Asn Leu Arg Pro Phe Thr Leu
785                 790                 795

TAC CGC ATC GAT ATC CAC AGC TGC AAC CAC GAG GCT GAG AAG CTG        2484
Tyr Arg Ile Asp Ile His Ser Cys Asn His Glu Ala Glu Lys Leu
        800                 805                 810
```

-continued

| | |
|---|---|
| GGC TGC AGC GCC TCC AAC TTC GTC TTT GCA AGG ACT ATG CCC GCA<br>Gly Cys Ser Ala Ser Asn Phe Val Phe Ala Arg Thr Met Pro Ala<br>815                    820                    825 | 2529 |
| GAA GGA GCA GAT GAC ATT CCT GGG CCA GTG ACC TGG GAG CCA AGG<br>Glu Gly Ala Asp Asp Ile Pro Gly Pro Val Thr Trp Glu Pro Arg<br>830                    835                    840 | 2574 |
| CCT GAA AAC TCC ATC TTT TTA AAG TGG CCG GAA CCT GAG AAT CCC<br>Pro Glu Asn Ser Ile Phe Leu Lys Trp Pro Glu Pro Glu Asn Pro<br>845                    850                    855 | 2619 |
| AAT GGA TTG ATT CTA ATG TAT GAA ATA AAA TAC GGA TCA CAA GTT<br>Asn Gly Leu Ile Leu Met Tyr Glu Ile Lys Tyr Gly Ser Gln Val<br>860                    865                    870 | 2664 |
| GAG GAT CAG CGA GAA TGT GTG TCC AGA CAG GAA TAC AGG AAG TAT<br>Glu Asp Gln Arg Glu Cys Val Ser Arg Gln Glu Tyr Arg Lys Tyr<br>875                    880                    885 | 2709 |
| GGA GGG GCC AAG CTA AAC CGG CTA AAC CCG GGA AAC TAC ACA GCC<br>Gly Gly Ala Lys Leu Asn Arg Leu Asn Pro Gly Asn Tyr Thr Ala<br>890                    895                    900 | 2754 |
| CGG ATT CAG GCC ACA TCT CTC TCT GGG AAT GGG TCG TGG ACA GAT<br>Arg Ile Gln Ala Thr Ser Leu Ser Gly Asn Gly Ser Trp Thr Asp<br>905                    910                    915 | 2799 |
| CCT GTG TTC TTC TAT GTC CAG GCC AAA ACA GGA TAT GAA AAC TTC<br>Pro Val Phe Phe Tyr Val Gln Ala Lys Thr Gly Tyr Glu Asn Phe<br>920                    925                    930 | 2844 |
| ATC CAT CTG ATC ATC GCT CTG CCC GTC GCT GTC CTG TTG ATC GTG<br>Ile His Leu Ile Ile Ala Leu Pro Val Ala Val Leu Leu Ile Val<br>935                    940                    945 | 2889 |
| GGA GGG TTG GTG ATT ATG CTG TAC GTC TTC CAT AGA AAG AGA AAT<br>Gly Gly Leu Val Ile Met Leu Tyr Val Phe His Arg Lys Arg Asn<br>950                    955                    960 | 2934 |
| AAC AGC AGG CTG GGG AAT GGA GTG CTG TAT GCC TCT GTG AAC CCG<br>Asn Ser Arg Leu Gly Asn Gly Val Leu Tyr Ala Ser Val Asn Pro<br>965                    970                    975 | 2979 |
| GAG TAC TTC AGC GCT GCT GAT GTG TAC GTT CCT GAT GAG TGG GAG<br>Glu Tyr Phe Ser Ala Ala Asp Val Tyr Val Pro Asp Glu Trp Glu<br>980                    985                    990 | 3024 |
| GTG GCT CGG GAG AAG ATC ACC ATG AGC CGG GAA CTT GGG CAG GGG<br>Val Ala Arg Glu Lys Ile Thr Met Ser Arg Glu Leu Gly Gln Gly<br>995                    1000                1005 | 3069 |
| TCG TTT GGG ATG GTC TAT GAA GGA GTT GCC AAG GGT GTG GTG AAA<br>Ser Phe Gly Met Val Tyr Glu Gly Val Ala Lys Gly Val Val Lys<br>1010                 1015                1020 | 3114 |
| GAT GAA CCT GAA ACC AGA GTG GCC ATT AAA ACA GTG AAC GAG GCC<br>Asp Glu Pro Glu Thr Arg Val Ala Ile Lys Thr Val Asn Glu Ala<br>1025                 1030                1035 | 3159 |
| GCA AGC ATG CGT GAG AGG ATT GAG TTT CTC AAC GAA GCT TCT GTG<br>Ala Ser Met Arg Glu Arg Ile Glu Phe Leu Asn Glu Ala Ser Val<br>1040                 1045                1050 | 3204 |
| ATG AAG GAG TTC AAT TGT CAC CAT GTG GTG CGA TTG CTG GGT GTG<br>Met Lys Glu Phe Asn Cys His His Val Val Arg Leu Leu Gly Val<br>1055                 1060                1065 | 3249 |
| GTG TCC CAA GGC CAG CCA ACA CTG GTC ATC ATG GAA CTG ATG ACA<br>Val Ser Gln Gly Gln Pro Thr Leu Val Ile Met Glu Leu Met Thr<br>1070                 1075                1080 | 3294 |
| CGG GGC GAT CTC AAA AGT TAT CTC CGG TCT CTG AGG CCA GAA ATG<br>Arg Gly Asp Leu Lys Ser Tyr Leu Arg Ser Leu Arg Pro Glu Met<br>1085                 1090                1095 | 3339 |
| GAG AAT AAT CCA GTC CTA GCA CCT CCA AGC CTG AGC AAG ATG ATT<br>Glu Asn Asn Pro Val Leu Ala Pro Pro Ser Leu Ser Lys Met Ile | 3384 |

-continued

```
          1100                1105                1110
CAG ATG GGC GGA GAG ATT GCA GAC GGC ATG GCA TAC CTC AAC GCC          3429
Gln Met Ala Gly Glu Ile Ala Asp Gly Met Ala Tyr Leu Asn Ala
          1115                1120                1125

AAT AAG TTC GTC CAC AGA GAC CTT GCT GCC CGG AAT TGC ATG GTA          3474
Asn Lys Phe Val His Arg Asp Leu Ala Ala Arg Asn Cys Met Val
          1130                1135                1140

GCC GAA GAT TTC ACA GTC AAA ATC GGA GAT TTT GGT ATG ACG CGA          3519
Ala Glu Asp Phe Thr Val Lys Ile Gly Asp Phe Gly Met Thr Arg
          1145                1150                1155

GAT ATC TAT GAG ACA GAC TAT TAC CGG AAA GGA GGG AAA GGG CTG          3564
Asp Ile Tyr Glu Thr Asp Tyr Tyr Arg Lys Gly Gly Lys Gly Leu
          1160                1165                1170

CTG CCC GTG CGC TGG ATG TCT CCT GAG TCC CTC AAG GAT GGA GTC          3609
Leu Pro Val Arg Trp Met Ser Pro Glu Ser Leu Lys Asp Gly Val
          1175                1180                1185

TTC ACC ACT TAC TCG GAC GTC TGG TCC TTC GGG GTC GTC CTC TGG          3654
Phe Thr Thr Tyr Ser Asp Val Trp Ser Phe Gly Val Val Leu Trp
          1190                1195                1200

GAG ATC GCC ACA CTG GCC GAG CAG CCC TAC CAG GGC TTG TCC AAC          3699
Glu Ile Ala Thr Leu Ala Glu Gln Pro Tyr Gln Gly Leu Ser Asn
          1205                1210                1215

GAG CAA GTC CTT CGC TTC GTC ATG GAG GGC GGC CTT CTG GAC AAG          3744
Glu Gln Val Leu Arg Phe Val Met Glu Gly Gly Leu Leu Asp Lys
          1220                1225                1230

CCA GAC AAC TGT CCT GAC ATG CTG TTT GAA CTG ATG CGC ATG TGC          3789
Pro Asp Asn Cys Pro Asp Met Leu Phe Glu Leu Met Arg Met Cys
          1235                1240                1245

TGG CAG TAT AAC CCC AAG ATG AGG CCT TCC TTC CTG GAG ATC ATC          3834
Trp Gln Tyr Asn Pro Lys Met Arg Pro Ser Phe Leu Glu Ile Ile
          1250                1255                1260

AGC AGC ATC AAA GAG GAG ATG GAG CCT GGC TTC CGG GAG GTC TCC          3879
Ser Ser Ile Lys Glu Glu Met Glu Pro Gly Phe Arg Glu Val Ser
          1265                1270                1275

TTC TAC TAC AGC GAG GAG AAC AAG CTG CCC GAG CCG GAG GAG CTG          3924
Phe Tyr Tyr Ser Glu Glu Asn Lys Leu Pro Glu Pro Glu Glu Leu
          1280                1285                1290

GAC CTG GAG CCA GAG AAC ATG GAG AGC GTC CCC CTG GAC CCC TCG          3969
Asp Leu Glu Pro Glu Asn Met Glu Ser Val Pro Leu Asp Pro Ser
          1295                1300                1305

GCC TCC TCG TCC TCC CTG CCA CTG CCC GAC AGA CAC TCA GGA CAC          4014
Ala Ser Ser Ser Ser Leu Pro Leu Pro Asp Arg His Ser Gly His
          1310                1315                1320

AAG GCC GAG AAC GGC CCC GGC CCT GGG GTG CTG GTC CTC CGC GCC          4059
Lys Ala Glu Asn Gly Pro Gly Pro Gly Val Leu Val Leu Arg Ala
          1325                1330                1335

AGC TTC GAC GAG AGA CAG CCT TAC GCC CAC ATG AAC GGG GGC CGC          4104
Ser Phe Asp Glu Arg Gln Pro Tyr Ala His Met Asn Gly Gly Arg
          1340                1345                1350

AAG AAC GAG CGG GCC TTG CCG CTG CCC CAG TCT TCG ACC TGC TGA          4149
Lys Asn Glu Arg Ala Leu Pro Leu Pro Gln Ser Ser Thr Cys
          1355                1360                1365

TCCTTGGATC CTGAATCTGT GCAAACAGTA ACGTGTGCGC ACGCGCAGCG GGTGGGG      4209

GGAGAGAGAG TTTTAACAAT CCATTCACAA GCCTCCTGTA CCTCAGTGGA TCTTCAGT     4269

TGCCCTTGCT GCCCGCGGGA GACAGCTTCT CTGCAGTAAA ACACATTTGG GATGTTCC    4329

TTTTCAATAT GCAAGCAGCT TTTTATTCCC TGCCCAAACC CTTAACTGAC ATGGGCCT    4389

AAGAACCTTA ATGACAACAC TTAATAGCAA CAGAGCACTT GAGAACCAGT CTCCTCAC    4449
```

-continued

```
TGTCCCTGTC CTTCCCTGTT CTCCCTTTCT CTCTCCTCTC TGCTTCATAA CGGAAAAA          4509

ATTGCCACAA GTCCAGCTGG GAAGCCCTTT TTATCAGTTT GAGGAAGTGG CTGTCCCT          4569

GGCCCCATCC CACCACTGTA CACACCCGCC TGACACCGTG GGTCATTACA AAAAAACA          4629

TGGAGATGGA AATTTTTACC TTTATCTTTC ACCTTTCTAG GGACATGAAA TTTACAAA          4689

GCCATCGTTC ATCCAAGGCT GTTACCATTT TAACGCTGCC TAATTTTGCC AAAATCCT          4749

ACTTTCTCCC TCATCGGCCC GGCGCTGATT CCTCGTGTCC GGAGGCATGG GTGAGCAT          4809

CAGCTGGTTG CTCCATTTGA GAGACACGCT GGCGACACAC TCCGTCCATC CGACTGCC          4869

TGCTGTGCTG CTCAAGGCCA CAGGCACACA GGTCTCAATG CTTCTGACTA GATTATTA          4929

TGGGGGAACT GGACACAATA GGTCTTTCTC TCAGTGAAGG TGGGGAGAAG CTGAACCG          4989
```

(2) INFORMATION FOR SEQ ID NO: 2:

(i) SEQUENCE CHARACTERISTICS:
        (A) LENGTH: 1367 amino acids
        (B) TYPE: amino acid
        (D) TOPOLOGY: linear (xi) SEQUENCE DESCRIPTION: SEQ ID NO: 2:

```
Met Lys Ser Gly Ser Gly Gly Ser Pro Thr Ser Leu Trp Gly
  1               5                  10                  15

Leu Leu Phe Leu Ser Ala Ala Leu Ser Leu Trp Pro Thr Ser Gly
                 20                  25                  30

Glu Ile Cys Gly Pro Gly Ile Asp Ile Arg Asn Asp Tyr Gln Gln
                 35                  40                  45

Leu Lys Arg Leu Glu Asn Cys Thr Val Ile Glu Gly Tyr Leu His
                 50                  55                  60

Ile Leu Leu Ile Ser Lys Ala Glu Asp Tyr Arg Ser Tyr Arg Phe
                 65                  70                  75

Pro Lys Leu Thr Val Ile Thr Glu Tyr Leu Leu Leu Phe Arg Val
                 80                  85                  90

Ala Gly Leu Glu Ser Leu Gly Asp Leu Phe Pro Asn Leu Thr Val
                 95                 100                 105

Ile Arg Gly Trp Lys Leu Phe Tyr Asn Tyr Ala Leu Val Ile Phe
                110                 115                 120

Glu Met Thr Asn Leu Lys Asp Ile Gly Leu Tyr Asn Leu Arg Asn
                125                 130                 135

Ile Thr Arg Gly Ala Ile Arg Ile Glu Lys Asn Ala Asp Leu Cys
                140                 145                 150

Tyr Leu Ser Thr Val Asp Trp Ser Leu Ile Leu Asp Ala Val Ser
                155                 160                 165

Asn Asn Tyr Ile Val Gly Asn Lys Pro Pro Lys Glu Cys Gly Asp
                170                 175                 180

Leu Cys Pro Gly Thr Met Glu Glu Lys Pro Met Cys Glu Lys Thr
                185                 190                 195

Thr Ile Asn Asn Glu Tyr Asn Tyr Arg Cys Trp Thr Thr Asn Arg
                200                 205                 210

Cys Gln Lys Met Cys Pro Ser Thr Cys Gly Lys Arg Ala Cys Thr
                215                 220                 225

Glu Asn Asn Glu Cys Cys His Pro Glu Cys Leu Gly Ser Cys Ser
                230                 235                 240

Ala Pro Asp Asn Asp Thr Ala Cys Val Ala Cys Arg His Tyr Tyr
                245                 250                 255
```

| | | | | | | | | | | | |
|---|---|---|---|---|---|---|---|---|---|---|---|
| Tyr | Ala | Gly | Val | Cys | Val | Pro | Ala | Cys | Pro | Pro | Asn | Thr | Tyr | Arg |
| | | | 260 | | | | | 265 | | | | | 270 | |

Tyr Ala Gly Val Cys Val Pro Ala Cys Pro Pro Asn Thr Tyr Arg
                260                 265                 270

Phe Glu Gly Trp Arg Cys Val Asp Arg Asp Phe Cys Ala Asn Ile
                275                 280                 285

Leu Ser Ala Glu Ser Ser Asp Ser Glu Gly Phe Val Ile His Asp
                290                 295                 300

Gly Glu Cys Met Gln Glu Cys Pro Ser Gly Phe Ile Arg Asn Gly
                305                 310                 315

Ser Gln Ser Met Tyr Cys Ile Pro Cys Glu Gly Pro Cys Pro Lys
                320                 325                 330

Val Cys Glu Glu Glu Lys Lys Thr Lys Thr Ile Asp Ser Val Thr
                335                 340                 345

Ser Ala Gln Met Leu Gln Gly Cys Thr Ile Phe Lys Gly Asn Leu
                350                 355                 360

Leu Ile Asn Ile Arg Arg Gly Asn Asn Ile Ala Ser Glu Leu Glu
                365                 370                 375

Asn Phe Met Gly Leu Ile Glu Val Val Thr Gly Tyr Val Lys Ile
                380                 385                 390

Arg His Ser His Ala Leu Val Ser Leu Ser Phe Leu Lys Asn Leu
                395                 400                 405

Arg Leu Ile Leu Gly Glu Glu Gln Leu Glu Gly Asn Tyr Ser Phe
                410                 415                 420

Tyr Val Leu Asp Asn Gln Asn Leu Gln Gln Leu Trp Asp Trp Asp
                425                 430                 435

His Arg Asn Leu Thr Ile Lys Ala Gly Lys Met Tyr Phe Ala Phe
                440                 445                 450

Asn Pro Lys Leu Cys Val Ser Glu Ile Tyr Arg Met Glu Glu Val
                455                 460                 465

Thr Gly Thr Lys Gly Arg Gln Ser Lys Gly Asp Ile Asn Thr Arg
                470                 475                 480

Asn Asn Gly Glu Arg Ala Ser Cys Glu Ser Asp Val Leu His Phe
                485                 490                 495

Thr Ser Thr Thr Thr Ser Lys Asn Arg Ile Ile Ile Thr Trp His
                500                 505                 510

Arg Tyr Arg Pro Pro Asp Tyr Arg Asp Leu Ile Ser Phe Thr Val
                515                 520                 525

Tyr Tyr Lys Glu Ala Pro Phe Lys Asn Val Thr Glu Tyr Asp Gly
                530                 535                 540

Gln Asp Ala Cys Gly Ser Asn Ser Trp Asn Met Val Asp Val Asp
                545                 550                 555

Leu Pro Pro Asn Lys Asp Val Glu Pro Gly Ile Leu Leu His Gly
                560                 565                 570

Leu Lys Pro Trp Thr Gln Tyr Ala Val Tyr Val Lys Ala Val Thr
                575                 580                 585

Leu Thr Met Val Glu Asn Asp His Ile Arg Gly Ala Lys Ser Glu
                590                 595                 600

Ile Leu Tyr Ile Arg Thr Asn Ala Ser Val Pro Ser Ile Pro Leu
                605                 610                 615

Asp Val Leu Ser Ala Ser Asn Ser Ser Gln Leu Ile Val Lys
                620                 625                 630

Trp Asn Pro Pro Ser Leu Pro Asn Gly Asn Leu Ser Tyr Tyr Ile
                635                 640                 645

-continued

```
Val Arg Trp Gln Arg Gln Pro Gln Asp Gly Tyr Leu Tyr Arg His
            650                 655                 660

Asn Tyr Cys Ser Lys Asp Lys Ile Pro Ile Arg Lys Tyr Ala Asp
            665                 670                 675

Gly Thr Ile Asp Ile Glu Val Thr Glu Asn Pro Lys Thr Glu
            680                 685                 690

Val Cys Gly Gly Glu Lys Gly Pro Cys Cys Ala Cys Pro Lys Thr
            695                 700                 705

Glu Ala Glu Lys Gln Ala Glu Lys Glu Ala Glu Tyr Arg Lys
            710                 715                 720

Val Phe Glu Asn Phe Leu His Asn Ser Ile Phe Val Pro Arg Pro
            725                 730                 735

Glu Arg Lys Arg Arg Asp Val Met Gln Val Ala Asn Thr Thr Met
            740                 745                 750

Ser Ser Arg Ser Arg Asn Thr Thr Ala Ala Asp Thr Tyr Asn Ile
            755                 760                 765

Thr Asp Pro Glu Glu Leu Glu Thr Glu Tyr Pro Phe Phe Glu Ser
            770                 775                 780

Arg Val Asp Asn Lys Glu Arg Thr Val Ile Ser Asn Leu Arg Pro
            785                 790                 795

Phe Thr Leu Tyr Arg Ile Asp Ile His Ser Cys Asn His Glu Ala
            800                 805                 810

Glu Lys Leu Gly Cys Ser Ala Ser Asn Phe Val Phe Ala Arg Thr
            815                 820                 825

Met Pro Ala Glu Gly Ala Asp Asp Ile Pro Gly Pro Val Thr Trp
            830                 835                 840

Glu Pro Arg Pro Glu Asn Ser Ile Phe Leu Lys Trp Pro Glu Pro
            845                 850                 855

Glu Asn Pro Asn Gly Leu Ile Leu Met Tyr Glu Ile Lys Tyr Gly
            860                 865                 870

Ser Gln Val Glu Asp Gln Arg Glu Cys Val Ser Arg Gln Glu Tyr
            875                 880                 885

Arg Lys Tyr Gly Gly Ala Lys Leu Asn Arg Leu Asn Pro Gly Asn
            890                 895                 900

Tyr Thr Ala Arg Ile Gln Ala Thr Ser Leu Ser Gly Asn Gly Ser
            905                 910                 915

Trp Thr Asp Pro Val Phe Phe Tyr Val Gln Ala Lys Thr Gly Tyr
            920                 925                 930

Glu Asn Phe Ile His Leu Ile Ile Ala Leu Pro Val Ala Val Leu
            935                 940                 945

Leu Ile Val Gly Gly Leu Val Ile Met Leu Tyr Val Phe His Arg
            950                 955                 960

Lys Arg Asn Asn Ser Arg Leu Gly Asn Gly Val Leu Tyr Ala Ser
            965                 970                 975

Val Asn Pro Glu Tyr Phe Ser Ala Ala Asp Val Tyr Val Pro Asp
            980                 985                 990

Glu Trp Glu Val Ala Arg Glu Lys Ile Thr Met Ser Arg Glu Leu
            995                1000                1005

Gly Gln Gly Ser Phe Gly Met Val Tyr Glu Gly Val Ala Lys Gly
           1010                1015                1020

Val Val Lys Asp Glu Pro Glu Thr Arg Val Ala Ile Lys Thr Val
           1025                1030                1035

Asn Glu Ala Ala Ser Met Arg Glu Arg Ile Glu Phe Leu Asn Glu
```

-continued

```
                              1040                1045                1050

Ala Ser Val Met Lys Glu Phe Asn Cys His His Val Val Arg Leu
                              1055                1060                1065

Leu Gly Val Val Ser Gln Gly Gln Pro Thr Leu Val Ile Met Glu
                              1070                1075                1080

Leu Met Thr Arg Gly Asp Leu Lys Ser Tyr Leu Arg Ser Leu Arg
                              1085                1090                1095

Pro Glu Met Glu Asn Asn Pro Val Leu Ala Pro Pro Ser Leu Ser
                              1100                1105                1110

Lys Met Ile Gln Met Ala Gly Glu Ile Ala Asp Gly Met Ala Tyr
                              1115                1120                1125

Leu Asn Ala Asn Lys Phe Val His Arg Asp Leu Ala Ala Arg Asn
                              1130                1135                1140

Cys Met Val Ala Glu Asp Phe Thr Val Lys Ile Gly Asp Phe Gly
                              1145                1150                1155

Met Thr Arg Asp Ile Tyr Glu Thr Asp Tyr Tyr Arg Lys Gly Gly
                              1160                1165                1170

Lys Gly Leu Leu Pro Val Arg Trp Met Ser Pro Glu Ser Leu Lys
                              1175                1180                1185

Asp Gly Val Phe Thr Thr Tyr Ser Asp Val Trp Ser Phe Gly Val
                              1190                1195                1200

Val Leu Trp Glu Ile Ala Thr Leu Ala Glu Gln Pro Tyr Gln Gly
                              1205                1210                1215

Leu Ser Asn Glu Gln Val Leu Arg Phe Val Met Glu Gly Gly Leu
                              1220                1225                1230

Leu Asp Lys Pro Asp Asn Cys Pro Asp Met Leu Phe Glu Leu Met
                              1235                1240                1245

Arg Met Cys Trp Gln Tyr Asn Pro Lys Met Arg Pro Ser Phe Leu
                              1250                1255                1260

Glu Ile Ile Ser Ser Ile Lys Glu Glu Met Glu Pro Gly Phe Arg
                              1265                1270                1275

Glu Val Ser Phe Tyr Tyr Ser Glu Glu Asn Lys Leu Pro Glu Pro
                              1280                1285                1290

Glu Glu Leu Asp Leu Glu Pro Glu Asn Met Glu Ser Val Pro Leu
                              1295                1300                1305

Asp Pro Ser Ala Ser Ser Ser Leu Pro Leu Pro Asp Arg His
                              1310                1315                1320

Ser Gly His Lys Ala Glu Asn Gly Pro Gly Pro Gly Val Leu Val
                              1325                1330                1335

Leu Arg Ala Ser Phe Asp Glu Arg Gln Pro Tyr Ala His Met Asn
                              1340                1345                1350

Gly Gly Arg Lys Asn Glu Arg Ala Leu Pro Leu Pro Gln Ser Ser
                              1355                1360                1365

Thr Cys
```

(2) INFORMATION FOR SEQ ID NO: 3:

(i) SEQUENCE CHARACTERISTICS:
        (A) LENGTH: 4993 base pairs
        (B) TYPE: nucleic acid
        (C) STRANDEDNESS: double
        (D) TOPOLOGY: linear (xi) SEQUENCE DESCRIPTION: SEQ ID NO: 3:

```
TTTTTTTTTT TTTTGAGAAA GGGAATTTCA TCCCAAATAA AAGGA ATG AAG TCT        54
```

-continued

```
                                    Met Lys Ser
                                     1
GGC TCC GGA GGA GGG TCC CCG ACC TCG CTG TGG GGG CTC CTG TTT          99
Gly Ser Gly Gly Gly Ser Pro Thr Ser Leu Trp Gly Leu Leu Phe
     5                  10                  15

CTC TCC GCC GCG CTC TCG CTC TGG CCG ACG AGT GGA GAA ATC TGC         144
Leu Ser Ala Ala Leu Ser Leu Trp Pro Thr Ser Gly Glu Ile Cys
 20                  25                  30

GGG CCA GGC ATC GAC ATC CGC AAC GAC TAT CAG CAG CTG AAG CGC         189
Gly Pro Gly Ile Asp Ile Arg Asn Asp Tyr Gln Gln Leu Lys Arg
         35                  40                  45

CTG GAG AAC TGC ACG GTG ATC GAG GGC TAC CTC CAC ATC CTG CTC         234
Leu Glu Asn Cys Thr Val Ile Glu Gly Tyr Leu His Ile Leu Leu
 50                  55                  60

ATC TCC AAG GCC GAG GAC TAC CGC AGC TAC CGC TTC CCC AAG CTC         279
Ile Ser Lys Ala Glu Asp Tyr Arg Ser Tyr Arg Phe Pro Lys Leu
 65                  70                  75

ACG GTC ATT ACC GAG TAC TTG CTG CTG TTC CGA GTG GCT GGC CTC         324
Thr Val Ile Thr Glu Tyr Leu Leu Leu Phe Arg Val Ala Gly Leu
 80                  85                  90

GAG AGC CTC GGA GAC CTC TTC CCC AAC CTC ACG GTC ATC CGC GGC         369
Glu Ser Leu Gly Asp Leu Phe Pro Asn Leu Thr Val Ile Arg Gly
 95                 100                 105

TGG AAA CTC TTC TAC AAC TAC GCC CTG GTC ATC TTC GAG ATG ACC         414
Trp Lys Leu Phe Tyr Asn Tyr Ala Leu Val Ile Phe Glu Met Thr
110                 115                 120

AAT CTC AAG GAT ATT GGG CTT TAC AAC CTG AGG AAC ATT ACT CGG         459
Asn Leu Lys Asp Ile Gly Leu Tyr Asn Leu Arg Asn Ile Thr Arg
125                 130                 135

GGG GCC ATC AGG ATT GAG AAA AAT GCT GAC CTC TGT TAC CTC TCC         504
Gly Ala Ile Arg Ile Glu Lys Asn Ala Asp Leu Cys Tyr Leu Ser
140                 145                 150

ACT GTG GAC TGG TCC CTG ATC CTG GAT GCG GTG TCC AAT AAC TAC         549
Thr Val Asp Trp Ser Leu Ile Leu Asp Ala Val Ser Asn Asn Tyr
155                 160                 165

ATT GTG GGG AAT AAG CCC CCA AAG GAA TGT GGG GAC CTG TGT CCA         594
Ile Val Gly Asn Lys Pro Pro Lys Glu Cys Gly Asp Leu Cys Pro
170                 175                 180

GGG ACC ATG GAG GAG AAG CCG ATG TGT GAG AAG ACC ACC ATC AAC         639
Gly Thr Met Glu Glu Lys Pro Met Cys Glu Lys Thr Thr Ile Asn
185                 190                 195

AAT GAG TAC AAC TAC CGC TGC TGG ACC ACA AAC CGC TGC CAG AAA         684
Asn Glu Tyr Asn Tyr Arg Cys Trp Thr Thr Asn Arg Cys Gln Lys
200                 205                 210

ATG TGC CCA AGC ACG TGT GGG AAG CGG GCG TGC ACC GAG AAC AAT         729
Met Cys Pro Ser Thr Cys Gly Lys Arg Ala Cys Thr Glu Asn Asn
215                 220                 225

GAG TGC TGC CAC CCC GAG TGC CTG GGC AGC TGC AGC GCG CCT GAC         774
Glu Cys Cys His Pro Glu Cys Leu Gly Ser Cys Ser Ala Pro Asp
230                 235                 240

AAC GAC ACG GCC TGT GTA GCT TGC CGC CAC TAC TAC TAT GCC GGT         819
Asn Asp Thr Ala Cys Val Ala Cys Arg His Tyr Tyr Tyr Ala Gly
245                 250                 255

GTC TGT GTG CCT GCC TGC CCG CCC AAC ACC TAC AGG TTT GAG GGC         864
Val Cys Val Pro Ala Cys Pro Pro Asn Thr Tyr Arg Phe Glu Gly
260                 265                 270

TGG CGC TGT GTG GAC CGT GAC TTC TGC GCC AAC ATC CTC AGC GCC         909
Trp Arg Cys Val Asp Arg Asp Phe Cys Ala Asn Ile Leu Ser Ala
275                 280                 285
```

```
GAG AGC AGC GAC TCC GAG GGG TTT GTG ATC CAC GAC GGC GAG TGC         954
Glu Ser Ser Asp Ser Glu Gly Phe Val Ile His Asp Gly Glu Cys
290             295                 300

ATG CAG GAG TGC CCC TCG GGC TTC ATC CGC AAC GGC AGC CAG AGC         999
Met Gln Glu Cys Pro Ser Gly Phe Ile Arg Asn Gly Ser Gln Ser
    305             310                 315

ATG TAC TGC ATC CCT TGT GAA GGT CCT TGC CCG AAG GTC TGT GAG        1044
Met Tyr Cys Ile Pro Cys Glu Gly Pro Cys Pro Lys Val Cys Glu
320             325                 330

GAA GAA AAG AAA ACA AAG ACC ATT GAT TCT GTT ACT TCT GCT CAG        1089
Glu Glu Lys Lys Thr Lys Thr Ile Asp Ser Val Thr Ser Ala Gln
    335             340                 345

ATG CTC CAA GGA TGC ACC ATC TTC AAG GGC AAT TTG CTC ATT AAC        1134
Met Leu Gln Gly Cys Thr Ile Phe Lys Gly Asn Leu Leu Ile Asn
350             355                 360

ATC CGA CGG GGG AAT AAC ATT GCT TCA GAG CTG GAG AAC TTC ATG        1179
Ile Arg Arg Gly Asn Asn Ile Ala Ser Glu Leu Glu Asn Phe Met
    365             370                 375

GGG CTC ATC GAG GTG GTG ACG GGC TAC GTG AAG ATC CGC CAT TCT        1224
Gly Leu Ile Glu Val Val Thr Gly Tyr Val Lys Ile Arg His Ser
380             385                 390

CAT GCC TTG GTC TCC TTG TCC TTC CTA AAA AAC CTT CGC CTC ATC        1269
His Ala Leu Val Ser Leu Ser Phe Leu Lys Asn Leu Arg Leu Ile
    395             400                 405

CTA GGA GAG GAG CAG CTA GAA GGG AAT TAC TCC TTC TAC GTC CTC        1314
Leu Gly Glu Glu Gln Leu Glu Gly Asn Tyr Ser Phe Tyr Val Leu
410             415                 420

GAC AAC CAG AAC TTG CAG CAA CTG TGG GAC TGG GAC CAC CGC AAC        1359
Asp Asn Gln Asn Leu Gln Gln Leu Trp Asp Trp Asp His Arg Asn
    425             430                 435

CTG ACC ATC AAA GCA GGG AAA ATG TAC TTT GCT TTC AAT CCC AAA        1404
Leu Thr Ile Lys Ala Gly Lys Met Tyr Phe Ala Phe Asn Pro Lys
440             445                 450

TTA TGT GTT TCC GAA ATT TAC CGC ATG GAG GAA GTG ACG GGG ACT        1449
Leu Cys Val Ser Glu Ile Tyr Arg Met Glu Glu Val Thr Gly Thr
    455             460                 465

AAA GGG CGC CAA AGC AAA GGG GAC ATA AAC ACC AGG AAC AAC GGG        1494
Lys Gly Arg Gln Ser Lys Gly Asp Ile Asn Thr Arg Asn Asn Gly
470             475                 480

GAG AGA GCC TCC TGT GAA AGT GAC GTC CTG CAT TTC ACC TCC ACC        1539
Glu Arg Ala Ser Cys Glu Ser Asp Val Leu His Phe Thr Ser Thr
    485             490                 495

ACC ACG TCG AAG AAT CGC ATC ATC ATA ACC TGG CAC CGG CCG GTA        1584
Thr Thr Ser Lys Asn Arg Ile Ile Ile Thr Trp His Arg Pro Val
500             505                 510

CCG GCC CCC T GACTACAGGG ATCTCATCAG CTTCACCGTT TACTACAAGG          1634
Pro Ala Pro
    515

AAGCACCCTT TAAGAATGTC ACAGAGTATG ATGGGCAGGA TGCCTGCGGC TCCAACAG    1694

GGAACATGGT GGACGTGGAC CTCCCGCCCA ACAAGGACGT GGAGCCCGGC ATCTTACT    1754

ATGGGCTGAA GCCCTGGACT CAGTACGCCG TTTACGTCAA GGCTGTGACC CTCACCAT    1814

TGGAGAACGA CCATATCCGT GGGGCCAAGA GTGAGATCTT GTACATTCGC ACCAATGC    1874

CAGTTCCTTC CATTCCCTTG ACGTTCTTT CAGCATCGAA CTCCTCTTCT CAGTTAAT     1934

TGAAGTGGAA CCCTCCCTCT CTGCCCAACG GCAACCTGAG TTACTACATT GTGCGCTG    1994

AGCGGCAGCC TCAGGACGGC TACCTTTACC GGCACAATTA CTGCTCCAAA GACAAAAT    2054

CCATCAGGAA GTATGCCGAC GGCACCATCG ACATTGAGGA GGTCACAGAG AACCCCAA    2114
```

-continued

```
CTGAGGTGTG TGGTGGGGAG AAAGGGCCTT GCTGCGCCTG CCCCAAAACT GAAGCCGA      2174

AGCAGGCCGA GAAGGAGGAG GCTGAATACC GCAAAGTCTT TGAGAATTTC CTGCACAA      2234

CCATCTTCGT GCCCAGACCT GAAAGGAAGC GGAGAGATGT CATGCAAGTG GCCAACAC      2294

CCATGTCCAG CCGAAGCAGG AACACCACGG CCGCAGACAC CTACAACATC ACCGACCC      2354

AAGAGCTGGA GACAGAGTAC CCTTTCTTTG AGAGCAGAGT GGATAACAAG GAGAGAAC      2414

TCATTTCTAA CCTTCGGCCT TTCACATTGT ACCGCATCGA TATCCACAGC TGCAACCA      2474

AGGCTGAGAA GCTGGGCTGC AGCGCCTCCA ACTTCGTCTT TGCAAGGACT ATGCCCGC      2534

AAGGAGCAGA TGACATTCCT GGGCCAGTGA CCTGGGAGCC AAGGCCTGAA AACTCCAT      2594

TTTTAAAGTG GCCGGAACCT GAGAATCCCA ATGGATTGAT TCTAATGTAT GAAATAAA      2654

ACGGATCACA AGTTGAGGAT CAGCGAGAAT GTGTGTCCAG ACAGGAATAC AGGAAGTA      2714

GAGGGGCCAA GCTAAACCGG CTAAACCCGG GGAACTACAC AGCCCGGATT CAGGCCAC      2774

CTCTCTCTGG GAATGGGTCG TGGACAGATC CTGTGTTCTT CTATGTCCAG GCCAAAAC      2834

GATATGAAAA CTTCATCCAT CTGATCATCG CTCTGCCCGT CGCTGTCCTG TTGATCGT      2894

GAGGGTTGGT GATTATGCTG TACGTCTTCC ATAGAAAGAG AAATAACAGC AGGCTGGG      2954

ATGGAGTGCT GTATGCCTCT GTGAACCCGG AGTACTTCAG CGCTGCTGAT GTGTACGT      3014

CTGATGAGTG GGAGGTGGCT CGGGAGAAGA TCACCATGAG CCGGGAACTT GGGCAGGG      3074

CGTTTGGGAT GGTCTATGAA GGAGTTGCCA AGGGTGTGGT GAAAGATGAA CCTGAAAC      3134

GAGTGGCCAT TAAAACAGTG AACGAGGCCG CAAGCATGCG TGAGAGGATT GAGTTTCT      3194

ACGAAGCTTC TGTGATGAAG GAGTTCAATT GTCACCATGT GGTGCGATTG CTGGGTGT      3254

TGTCCCAAGG CCAGCCAACA CTGGTCATCA TGGAACTGAT GACACGGGGC GATCTCAA      3314

GTTATCTCCG GTCTCTGAGG CCAGAAATGG AGAATAATCC AGTCCTAGCA CCTCCAAG      3374

TGAGCAAGAT GATTCAGATG GGCGGAGAGA TTGCAGACGG CATGGCATAC CTCAACGC      3434

ATAAGTTCGT CCACAGAGAC CTTGCTGCCC GGAATTGCAT GGTAGCCGAA GATTTCAC      3494

TCAAAATCGG AGATTTTGGT ATGACGCGAG ATATCTATGA GACAGACTAT TACCGGAA      3554

GAGGGAAAGG GCTGCTGCCC GTGCGCTGGA TGTCTCCTGA GTCCCTCAAG GATGGAGT      3614

TCACCACTTA CTCGGACGTC TGGTCCTTCG GGGTCGTCCT CTGGGAGATC GCCACACT      3674

CCGAGCAGCC CTACCAGGGC TTGTCCAACG AGCAAGTCCT TCGCTTCGTC ATGGAGGG      3734

GCCTTCTGGA CAAGCCAGAC AACTGTCCTG ACATGCTGTT TGAACTGATG CGCATGTG      3794

GGCAGTATAA CCCCAAGATG AGGCCTTCCT TCCTGGAGAT CATCAGCAGC ATCAAAGA      3854

AGATGGAGCC TGGCTTCCGG GAGGTCTCCT TCTACTACAG CGAGGAGAAC AAGCTGCC      3914

AGCCGGAGGA GCTGGACCTG GAGCCAGAGA ACATGGAGAG CGTCCCCCTG GACCCCTC      3974

CCTCCTCGTC CTCCCTGCCA CTGCCCGACA GACACTCAGG ACACAAGGCC GAGAACGG      4034

CCGGCCCTGG GGTGCTGGTC CTCCGCGCCA GCTTCGACGA GAGACAGCCT TACGCCCA      4094

TGAACGGGGG CCGCAAGAAC GAGCGGGCCT TGCCGCTGCC CCAGTCTTCG ACCTGCTG      4154

CCTTGGATCC TGAATCTGTG CAAACAGTAA CGTGTGCGCA CGCGCAGCGG GGTGGGGG      4214

GAGAGAGAGT TTTAACAATC CATTCACAAG CCTCCTGTAC CTCAGTGGAT CTTCAGTT      4274

GCCCTTGCTG CCCGCGGGAG ACAGCTTCTC TGCAGTAAAA CACATTTGGG ATGTTCCT      4334

TTTCAATATG CAAGCAGCTT TTTATTCCCT GCCCAAACCC TTAACTGACA TGGGCCTT      4394

AGAACCTTAA TGACAACACT AATAGCAAC AGAGCACTTG AGAACCAGTC TCCTCACT      4454
```

-continued

```
GTCCCTGTCC TTCCCTGTTC TCCCTTTCTC TCTCCTCTCT GCTTCATAAC GGAAAAAT      4514

TTGCCACAAG TCCAGCTGGG AAGCCCTTTT TATCAGTTTG AGGAAGTGGC TGTCCCTG      4574

GCCCCATCCC ACCACTGTAC ACACCCGCCT GACACCGTGG GTCATTACAA AAAAACAC      4634

GGAGATGGAA ATTTTTACCT TTATCTTTCA CCTTTCTAGG GACATGAAAT TTACAAAG      4694

CCATCGTTCA TCCAAGGCTG TTACCATTTT AACGCTGCCT AATTTTGCCA AAATCCTG      4754

CTTTCTCCCT CATCGGCCCG GCGCTGATTC CTCGTGTCCG GAGGCATGGG TGAGCATG      4814

AGCTGGTTGC TCCATTTGAG AGACACGCTG GCGACACACT CCGTCCATCC GACTGCCC      4874

GCTGTGCTGC TCAAGGCCAC AGGCACACAG GTCTCAATGC TTCTGACTAG ATTATTAT      4934

GGGGGAACTG GACACAATAG GTCTTTCTCT CAGTGAAGGT GGGGAGAAGC TGAACCGG      4993
```

(2) INFORMATION FOR SEQ ID NO: 4:

(i) SEQUENCE CHARACTERISTICS:
        (A) LENGTH: 516 amino acids
        (B) TYPE: amino acid
        (D) TOPOLOGY: linear (xi) SEQUENCE DESCRIPTION: SEQ ID NO: 4:

```
Met Lys Ser Gly Ser Gly Gly Ser Pro Thr Ser Leu Trp Gly
  1               5                  10                  15

Leu Leu Phe Leu Ser Ala Ala Leu Ser Leu Trp Pro Thr Ser Gly
                 20                  25                  30

Glu Ile Cys Gly Pro Gly Ile Asp Ile Arg Asn Asp Tyr Gln Gln
                 35                  40                  45

Leu Lys Arg Leu Glu Asn Cys Thr Val Ile Glu Gly Tyr Leu His
                 50                  55                  60

Ile Leu Leu Ile Ser Lys Ala Glu Asp Tyr Arg Ser Tyr Arg Phe
 65                              70                      75

Pro Lys Leu Thr Val Ile Thr Glu Tyr Leu Leu Phe Arg Val
                 80                  85                  90

Ala Gly Leu Glu Ser Leu Gly Asp Leu Phe Pro Asn Leu Thr Val
                 95                 100                 105

Ile Arg Gly Trp Lys Leu Phe Tyr Asn Tyr Ala Leu Val Ile Phe
                110                 115                 120

Glu Met Thr Asn Leu Lys Asp Ile Gly Leu Tyr Asn Leu Arg Asn
                125                 130                 135

Ile Thr Arg Gly Ala Ile Arg Ile Glu Lys Asn Ala Asp Leu Cys
                140                 145                 150

Tyr Leu Ser Thr Val Asp Trp Ser Leu Ile Leu Asp Ala Val Ser
                155                 160                 165

Asn Asn Tyr Ile Val Gly Asn Lys Pro Pro Lys Glu Cys Gly Asp
                170                 175                 180

Leu Cys Pro Gly Thr Met Glu Glu Lys Pro Met Cys Glu Lys Thr
                185                 190                 195

Thr Ile Asn Asn Glu Tyr Asn Tyr Arg Cys Trp Thr Thr Asn Arg
                200                 205                 210

Cys Gln Lys Met Cys Pro Ser Thr Cys Gly Lys Arg Ala Cys Thr
                215                 220                 225

Glu Asn Asn Glu Cys Cys His Pro Glu Cys Leu Gly Ser Cys Ser
                230                 235                 240

Ala Pro Asp Asn Asp Thr Ala Cys Val Ala Cys Arg His Tyr Tyr
                245                 250                 255
```

-continued

```
Tyr Ala Gly Val Cys Val Pro Ala Cys Pro Pro Asn Thr Tyr Arg
            260                 265                 270

Phe Glu Gly Trp Arg Cys Val Asp Arg Asp Phe Cys Ala Asn Ile
            275                 280                 285

Leu Ser Ala Glu Ser Ser Asp Ser Glu Gly Phe Val Ile His Asp
            290                 295                 300

Gly Glu Cys Met Gln Glu Cys Pro Ser Gly Phe Ile Arg Asn Gly
            305                 310                 315

Ser Gln Ser Met Tyr Cys Ile Pro Cys Glu Gly Pro Cys Pro Lys
            320                 325                 330

Val Cys Glu Glu Glu Lys Lys Thr Lys Thr Ile Asp Ser Val Thr
            335                 340                 345

Ser Ala Gln Met Leu Gln Gly Cys Thr Ile Phe Lys Gly Asn Leu
            350                 355                 360

Leu Ile Asn Ile Arg Arg Gly Asn Asn Ile Ala Ser Glu Leu Glu
            365                 370                 375

Asn Phe Met Gly Leu Ile Glu Val Val Thr Gly Tyr Val Lys Ile
            380                 385                 390

Arg His Ser His Ala Leu Val Ser Leu Ser Phe Leu Lys Asn Leu
            395                 400                 405

Arg Leu Ile Leu Gly Glu Glu Gln Leu Glu Gly Asn Tyr Ser Phe
            410                 415                 420

Tyr Val Leu Asp Asn Gln Asn Leu Gln Gln Leu Trp Asp Trp Asp
            425                 430                 435

His Arg Asn Leu Thr Ile Lys Ala Gly Lys Met Tyr Phe Ala Phe
            440                 445                 450

Asn Pro Lys Leu Cys Val Ser Glu Ile Tyr Arg Met Glu Glu Val
            455                 460                 465

Thr Gly Thr Lys Gly Arg Gln Ser Lys Gly Asp Ile Asn Thr Arg
            470                 475                 480

Asn Asn Gly Glu Arg Ala Ser Cys Glu Ser Asp Val Leu His Phe
            485                 490                 495

Thr Ser Thr Thr Thr Ser Lys Asn Arg Ile Ile Ile Thr Trp His
            500                 505                 510

Arg Pro Val Pro Ala Pro
            515

(2) INFORMATION FOR SEQ ID NO: 5:

(i) SEQUENCE CHARACTERISTICS:
        (A) LENGTH: 486 amino acids
        (B) TYPE: amino acid
        (D) TOPOLOGY: linear (xi) SEQUENCE DESCRIPTION: SEQ ID NO: 5:

Glu Ile Cys Gly Pro Gly Ile Asp Ile Arg Asn Asp Tyr Gln Gln
 1               5                  10                  15

Leu Lys Arg Leu Glu Asn Cys Thr Val Ile Glu Gly Tyr Leu His
            20                  25                  30

Ile Leu Leu Ile Ser Lys Ala Glu Asp Tyr Arg Ser Tyr Arg Phe
            35                  40                  45

Pro Lys Leu Thr Val Ile Thr Glu Tyr Leu Leu Leu Phe Arg Val
            50                  55                  60

Ala Gly Leu Glu Ser Leu Gly Asp Leu Phe Pro Asn Leu Thr Val
            65                  70                  75
```

-continued

```
Ile Arg Gly Trp Lys Leu Phe Tyr Asn Tyr Ala Leu Val Ile Phe
             80                  85                  90

Glu Met Thr Asn Leu Lys Asp Ile Gly Leu Tyr Asn Leu Arg Asn
             95                 100                 105

Ile Thr Arg Gly Ala Ile Arg Ile Glu Lys Asn Ala Asp Leu Cys
            110                 115                 120

Tyr Leu Ser Thr Val Asp Trp Ser Leu Ile Leu Asp Ala Val Ser
            125                 130                 135

Asn Asn Tyr Ile Val Gly Asn Lys Pro Pro Lys Glu Cys Gly Asp
            140                 145                 150

Leu Cys Pro Gly Thr Met Glu Lys Pro Met Cys Glu Lys Thr
            155                 160                 165

Thr Ile Asn Asn Glu Tyr Asn Tyr Arg Cys Trp Thr Thr Asn Arg
            170                 175                 180

Cys Gln Lys Met Cys Pro Ser Thr Cys Gly Lys Arg Ala Cys Thr
            185                 190                 195

Glu Asn Asn Glu Cys Cys His Pro Glu Cys Leu Gly Ser Cys Ser
            200                 205                 210

Ala Pro Asp Asn Asp Thr Ala Cys Val Ala Cys Arg His Tyr Tyr
            215                 220                 225

Tyr Ala Gly Val Cys Val Pro Ala Cys Pro Pro Asn Thr Tyr Arg
            230                 235                 240

Phe Glu Gly Trp Arg Cys Val Asp Arg Asp Phe Cys Ala Asn Ile
            245                 250                 255

Leu Ser Ala Glu Ser Ser Asp Ser Glu Gly Phe Val Ile His Asp
            260                 265                 270

Gly Glu Cys Met Gln Glu Cys Pro Ser Gly Phe Ile Arg Asn Gly
            275                 280                 285

Ser Gln Ser Met Tyr Cys Ile Pro Cys Glu Gly Pro Cys Pro Lys
            290                 295                 300

Val Cys Glu Glu Glu Lys Lys Thr Lys Thr Ile Asp Ser Val Thr
            305                 310                 315

Ser Ala Gln Met Leu Gln Gly Cys Thr Ile Phe Lys Gly Asn Leu
            320                 325                 330

Leu Ile Asn Ile Arg Arg Gly Asn Asn Ile Ala Ser Glu Leu Glu
            335                 340                 345

Asn Phe Met Gly Leu Ile Glu Val Val Thr Gly Tyr Val Lys Ile
            350                 355                 360

Arg His Ser His Ala Leu Val Ser Leu Ser Phe Leu Lys Asn Leu
            365                 370                 375

Arg Leu Ile Leu Gly Glu Glu Gln Leu Glu Gly Asn Tyr Ser Phe
            380                 385                 390

Tyr Val Leu Asp Asn Gln Asn Leu Gln Gln Leu Trp Asp Trp Asp
            395                 400                 405

His Arg Asn Leu Thr Ile Lys Ala Gly Lys Met Tyr Phe Ala Phe
            410                 415                 420

Asn Pro Lys Leu Cys Val Ser Glu Ile Tyr Arg Met Glu Glu Val
            425                 430                 435

Thr Gly Thr Lys Gly Arg Gln Ser Lys Gly Asp Ile Asn Thr Arg
            440                 445                 450

Asn Asn Gly Glu Arg Ala Ser Cys Glu Ser Asp Val Leu His Phe
            455                 460                 465

Thr Ser Thr Thr Thr Ser Lys Asn Arg Ile Ile Ile Thr Trp His
```

```
                        470              475             480
Arg Pro Val Pro Ala Pro
                485

(2) INFORMATION FOR SEQ ID NO: 6:

(i) SEQUENCE CHARACTERISTICS:
        (A) LENGTH: 26
        (B) TYPE: nucleic acid
        (C) STRANDEDNESS: single
        (D) TOPOLOGY: linear (xi) SEQUENCE DESCRIPTION:  SEQ ID NO: 6:

GGATCCTAGA AATCTGCGGG CCAGGC                                          26

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: single
        (D) TOPOLOGY: linear (xi) SEQUENCE DESCRIPTION:  SEQ ID NO: 7:

TCAGGGGGCC GGTACCGGCC                                                 20
```

INDUCING RESISTANCE TO TUMOR GROWTH WITH SOLUBLE IGF-1 RECEPTOR

CROSS-REFERENCE TO RELATED APPLICATIONS

This patent application claims priority under 35 U.S.C. §119(e) to provisional patent application Ser. No. 60/006,699, filed Nov. 14, 1996, hereby incorporated in its entirety by reference.

REFERENCE TO GOVERNMENT GRANTS

This invention was funded by National Institute of Health Grants GM 33694 and CA 56309. The U.S. government may have certain rights in the invention.

FIELD OF THE INVENTION

The present invention relates to expression vectors that code for soluble type I insulin-like growth factor receptor (IGF-1R) which, when transfected into tumor cells, reverses the transformed phenotype, induces apoptosis, and inhibits tumorigenesis in syngeneic animals.

BACKGROUND OF THE INVENTION

It is well established that growth factors play a crucial role in the establishment and maintenance of the transformed phenotype. Evidence is rapidly accumulating that growth factor receptors also play a crucial role in the establishment and maintenance of transformed phenotypes.

The IGF-1R belongs to the family of tyrosine kinase growth factor receptors (Ullrich, et al., *Cell*, 1990, 61, 203), and is 70% homologous to the insulin growth factor I receptor (Ullrich, et al., *EMBO J.*, 1986, 5, 503). The IGF-1R activated by its ligands (IGF-1, IGF-2 and insulin at supraphysiological concentrations) has been known to be mitogenic in cell cultures. However, in growth-regulated cells, like 3T3 cells and human diploid fibroblasts, IGF-1, by itself, cannot sustain growth of cells in serum-free medium (SFM), but requires the cooperation of other growth factors, for instance PDGF and/or EGF, which, by themselves, also fail to induce a mitogenic response. Scher, et al., *Biochem. Biophys. Acta,* 1979, 560, 217; and Stiles, et al., *Proc. Natl. Acad. Sci. U.S.A.,* 1979, 76, 1279.

Recently, the importance of the IGF-1R in cell growth has been confirmed in vivo by the finding that mouse embryos with a targeted disruption of the IGF-1R and IGF-2 genes have a size at birth that is only 30% the size of wild type littermates. Liu, et al., *Cell, 1993, 75, 59*; and Baker, et al., *Cell,* 1993, 73, 73. 3T3-like cells derived from these mouse embryos devoid of IGF-1Rs (R⁻ cells) do not grow at all in SFM supplemented by a variety of growth factors, which can sustain the growth of cells derived from wild type littermate embryos (W cells) and other 3T3-cells. Sell, et al., *Mol. Cell. Biol.,* 1994, 14, 3604. R⁻ cells grow in 10% FBS at a rate that is roughly 40% the rate of W cells, with all phases of the cell cycle being equally elongated. Sell, et al., *Mol. Cell. Biol.,* 1994, 14, 3604. R⁻ cells are also refractory to transformation by SV40 large T antigen, by an activated ras or a combination of both (Sell, et al., *Proc. Natl. Acad. Sci. U.S.A.,* 1993, 90, 11217; and Sell, et al., *Mol. Cell. Biol.,* 1994, 14, 3604), or by overexpressed growth factor receptors, such as the EGF receptor (Coppola, et al., *Mol. Cell. Biol.,* 1994, 14, 4588), the PDGF β receptor (DeAngelis, et al., *J. Cell. Physiol.,* 1995, 164, 214) and the insulin receptor (Miura, et al., *Cancer Res.,* 1995, 55, 663), all conditions that readily transform cells from wild type littermate embryos or other 3T3-like cells with a physiological number of IGF-1Rs. Conversely, overexpression and/or constitutive activation of IGF-1R in a variety of cell types leads to ligand-dependent growth in SFM and to the establishment of a transformed phenotype. Kaleko, et al., *Mol. Cell. Biol.,* 1990, 10, 464; McCubrey, et al., *Blood,* 1991, 78, 921; Pietrzkowski, et al., *Mol. Cell. Biol.,* 1992, 12, 3883; Liu, et al., *Cell,* 1993, 75, 59; Sell, et al., *Mol. Cell. Biol.,* 1994, 14, 3604; Coppola, et al., *Mol. Cell. Biol.,* 1994, 14, 4588; and Surmacz, et al., *Exp. Cell Res.,* 1995, 218, 370.

The importance of the IGF-1 receptor in the control of cell proliferation is also supported by the observation that many cell types in culture are stimulated to grow by IGF-I (Goldring, et al., *Crit. Rev. Eukaryot. Gene Expr.,* 1991, 1, 301; and Baserga, et al., *Crit. Rev. Eukaryot. Gene Expr.,* 1993, 3, 47), and these cell types include human diploid fibroblasts, epithelial cells, smooth muscle cells, T lymphocytes, myeloid cells, chondrocytes, osteoblasts as well as the stem cells of the bone marrow. Using antisense expression vectors or antisense oligonucleotides to the IGF-1 receptor RNA, it has been shown that interference with IGF-1 receptor leads to inhibition of cell growth. The antisense strategy was successful in inhibiting cellular proliferation in several normal cell types and in human tumor cell lines. Baserga, *Cell,* 1994, 79, 927. Growth can also be inhibited using peptide analogues of IGF-1 (Pietrzkowski, et al., *Cell Growth & Diff.,* 1992, 3, 199; and Pietrzkowski, et al., *Mol. Cell. Biol.,* 1992, 12, 3883), or a vector expressing an antisense RNA to the IGF-1 RNA (Trojan, et al., *Science,* 1993, 259, 94). The IGF autocrine or paracrine loop is also involved in the growth promoting effect of other growth factors, hormones (for instance, growth hormone and estrogens), and oncogenes like SV40 T antigen and c-myb, and in tumor suppression, as in the case of WT1 (Baserga, *Cell,* 1994, 79, 927).

The important role of IGF-1R in the establishment and maintenance of the transformed phenotype is supported by other findings. Antisense oligonucleotides or antisense expression plasmids against either IGF-2 (Christophori, et al., *Nature,* 1994, 369, 414; and Rogler, et al., *J. Biol. Chem.,* 1994, 269, 13779), IGF-1 (Trojan, et al., *Proc. Natl. Acad. Sci. U.S.A.,* 1992, 89, 4874; and Trojan, et al., *Science,* 1993, 259, 94) or the IGF-1R (Sell, et al., *Proc. Natl. Acad. Sci. U.S.A.,* 1993, 90, 11217; Baserga, *Cell,* 1994, 79, 927; Resnicoff, et al., *Cancer Res.,* 1994, 54, 2218; Resnicoff, et al., *Cancer Res.,* 1994, 54, 4848; and Shapiro, et al., *J. Clin. Invest.,* 1994, 94, 1235), antibodies to the IGF-1R (Arteaga, et al., *Breast Canc. Res. Treatm.,* 1992, 22, 101; and Kalebic, et al., *Cancer Res.,* 1994, 54, 5531), and dominant negative mutants of the IGF-1R (Prager, et al., *Proc. Natl. Acad. Sci. U.S.A.,* 1994, 91, 2181; and Li, et al., *J. Biol. Chem.,* 1994, 269, 32558), can all reverse the transformed phenotype, inhibit tumorigenesis, and induce loss of the metastatic phenotype (Long, et al., *Cancer Res.,* 1995, 54, 1006). An overexpressed IGF-1R has been found to protect tumor cells in vitro from etoposide-induced apoptosis (Sell, et al., *Cancer Res.,* 1995, 55, 303) and, even more dramatically, that a decrease in IGF-1R levels below wild type levels caused massive apoptosis of tumor cells in vivo (Resnicoff, et al., *Cancer Res.,* 1995, 55, 2463).

Expression of an antisense RNA to the IGF-1R RNA in C6 rat glioblastoma cells not only abrogates tumorigenesis in syngeneic rats, but also causes complete regression of established wild type tumors. Resnicoff, et al., *Cancer Res.,* 1994, 54, 2218; and Resnicoff, et al., *Cancer Res.,* 1994, 54, 4848. Cells expressing an antisense RNA to the IGF-1R RNA or cells pre-incubated with antisense oligonucleotides to the IGF-1R RNA completely lose their tumorigenicity when injected in either syngeneic or nude mice. Resnicoff, et al., *Cancer Res.*, 1994, 54, 2218; and Resnicoff, et al., *Cancer Res.*, 1994, 54, 4848. The injected cells were suspected of undergoing apoptosis or some form of cell death. Dying cells, however, are very difficult to demonstrate, because dying cells, especially in vivo, disappear very rapidly, and one is left with nothing to examine.

Tumors and other neoplastic tissues are known to undergo apoptosis spontaneously or in response to treatment. Examples include several types of leukemia, non-Hodgkin's lymphoma, prostate tumor, pancreatic cancer, basal and squamous cell carcinoma, mammary tumor, breast cancer, and fat pad sarcoma. Several anticancer drugs have been shown to induce apoptosis in target cells. Buttyan, et al., *Mol. Cell. Biol.*, 1989, 9, 3473; Kaufmann, *Cancer Res.*, 1989, 49, 5870; and Barry, et al., *Biochem. Pharmacol.*, 1990, 40, 2353. Certain mildly adverse conditions can result in the injured cell dying by programmed cell death, including hyperthermia, hypothermia, ischemia, and exposure to irradiation, toxins, and chemicals. It should be noted that many of these treatments will also result in necrosis at higher doses, suggesting that mild injury to a cell might induce a cell to commit suicide, perhaps to prevent the inheritance of a mutation, while exposure to severe conditions leads directly to cell death by necrosis.

Apoptosis refers to cell death, including, but not limited to, regression of primary and metastatic tumors. Apoptosis is a programmed cell death which is a widespread phenomenon that plays a crucial role in the myriad of physiological and pathological processes. There exists a homeostatic control of cell number thought to result from the dynamic balance between cell proliferation and cell death. In contrast, necrosis refers to an accidental cell death which is the cell's response to a variety of harmful conditions and toxic substances.

Apoptosis, morphologically distinct from necrosis, is a spontaneous form of cell death that occurs in many different tissues under various conditions. This type of cell death typically occurs in scattered cells and progresses so rapidly that it is difficult to observe.

The cell death process of apoptosis occurs in two stages. The cell undergoes nuclear and cytoplasmic condensation, eventually breaking into a number of membrane-bound fragments containing structurally intact apoptotic bodies, which are phagocytosed by neighboring cells and rapidly degraded. Apoptosis is observed in many different tissues, healthy and neoplastic, adult and embryonic. Death occurs spontaneously, or is induced by physiological or noxious agents. Apoptosis is a basic physiological process that plays a major role in the regulation of cell populations.

The death process is difficult to observe due to the rapidity of the process and the reduced amount of inflammation. For these reasons, quantification of apoptosis is often difficult. A method of measuring the duration of the histologically visible stages of apoptosis (3 hours in normal rat liver) and present a formula by which to calculate the cell loss rate by apoptosis. Bursch, et al., *Carcinogenesis*, 1990, 11, 847.

Nonetheless, testing agents such as growth factors and growth factor receptors for their ability to maintain or suppress transformed phenotypes remains difficult. In order to obtain an accurate account of the tumor suppressive ability, testing should be performed in vivo. Therapies such as direct injection or implantation of toxic treatments, tissue samples, and chemotherapy often jeopardizes the overall health of the patient. The present invention provides a method of inducing resistance to tumor growth with markedly reduced side effects to the patient.

SUMMARY OF THE INVENTION

The present invention relates to isolated soluble IGF-1R proteins.

The invention relates to isolated soluble IGF-1R proteins having amino acid sequence set forth in SEQ ID NO:5, or SEQ ID NO:4, or fragments thereof.

The invention relates to pharmaceutical compositions comprising isolated soluble IGF-1R in combination with a pharmaceutically acceptable carrier.

The invention relates to isolated nucleic acid molecules comprising nucleic acid sequences encoding soluble IGF-1R having an amino acid sequence set forth in SEQ ID NO:5, or SEQ ID NO:4, or fragments thereof.

The invention relates to pharmaceutical compositions comprising nucleic acid molecules comprising nucleic acid sequences encoding soluble IGF-1R having an amino acid sequence set forth in SEQ ID NO:5, or SEQ ID NO:4, or fragments thereof, in combination with a pharmaceutically acceptable carrier.

The invention relates to isolated nucleic acid molecules consisting of sequences encoding soluble IGF-1R having an amino acid sequence set forth in SEQ ID NO:5, or SEQ ID NO:4, or fragments thereof.

The invention relates to a recombinant expression vector comprising nucleic acid molecules having nucleic acid sequences encoding soluble IGF-1R having an amino acid sequence set forth in SEQ ID NO:5, or SEQ ID NO:4, or fragments thereof.

The invention relates to a host cell comprising a recombinant expression vector comprising nucleic acid molecules comprising nucleic acid sequences encoding soluble IGF-1R having an amino acid sequence set forth in SEQ ID NO:5, or SEQ ID NO:4, or fragments thereof.

The invention relates to methods of inducing apoptosis in tumor cells by contacting tumor cells with soluble IGF-1R.

The invention relates to methods of inducing apoptosis in tumor cells by transfecting tumor cells with nucleic acid molecules encoding soluble IGF-1R.

The invention relates to methods of treating individuals who have tumors comprising administering to such individuals a therapeutically effective amount of soluble IGF-1R.

The invention relates to methods of inducing apoptosis in tumor cells by introducing into the tumor cells a nucleic acid molecule comprising a nucleotide sequence encoding soluble IGF-1R operably linked to regulatory elements functional in the tumor cells wherein, upon introduction into the tumor cell, the nucleotide sequence that encodes soluble IGF-1R is expressed.

The invention relates to methods of treating individuals who have tumors comprising administering to such individuals a therapeutically effective amount of a nucleic acid molecules encoding soluble IGF-1R operably linked to regulatory sequences that function in tumor cells.

The invention relates to a method of inducing resistance to tumor growth in an individual comprising administering soluble IGF-1R for a therapeutically effective time.

The invention relates to a method of inducing resistance to tumor growth in an individual comprising providing a tumor cell culture supplemented with soluble IGF-1R in a diffusion chamber and inserting said chamber into an individual for a therapeutically effective time.

The invention relates to a method of inducing resistance to tumor growth in an individual comprising providing a tumor cell culture in a diffusion chamber and inserting said chamber into an individual for a therapeutically effective time, wherein the tumor cells are transfected with a gene construct comprising a nucleic acid molecule encoding soluble IGF-1R that has an amino acid sequence set forth in SEQ ID NO:5, or SEQ ID NO:4, or a fragment thereof.

The invention relates to diffusion chambers comprising tumor cells with medium supplemented with soluble IGF-1R that has an amino acid sequence set forth in SEQ ID NO:5, or SEQ ID NO:4, or a fragment thereof.

The invention relates to diffusion chambers comprising tumor cells with medium, wherein the tumor cells are transfected with a gene construct comprising nucleic acid molecule encoding soluble IGF-1R that has an amino acid sequence set forth in SEQ ID NO:5, or SEQ ID NO:4, or a fragment thereof.

BRIEF DESCRIPTION OF THE FIGURES

Figure 1A:
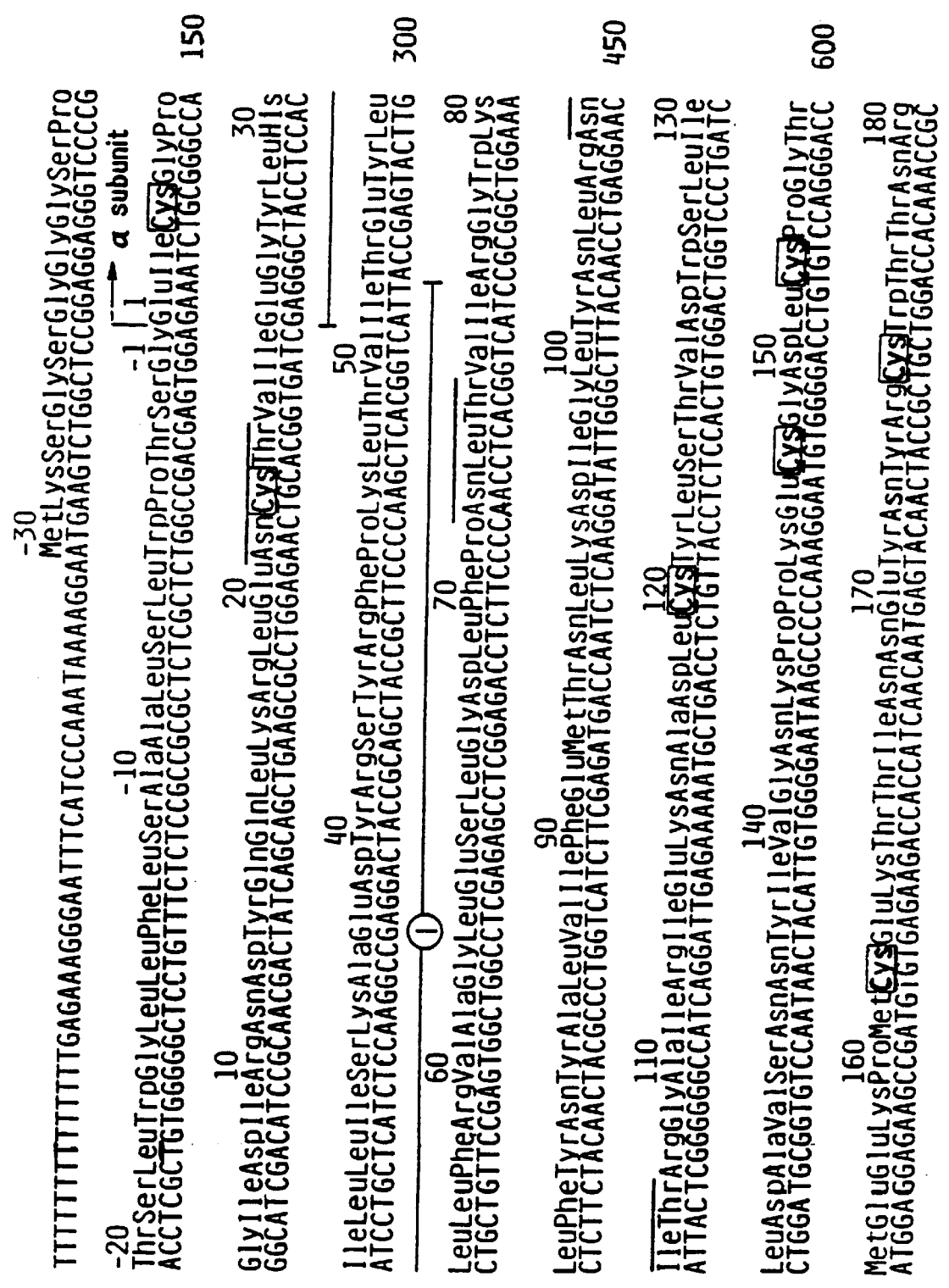
Figure 1D:
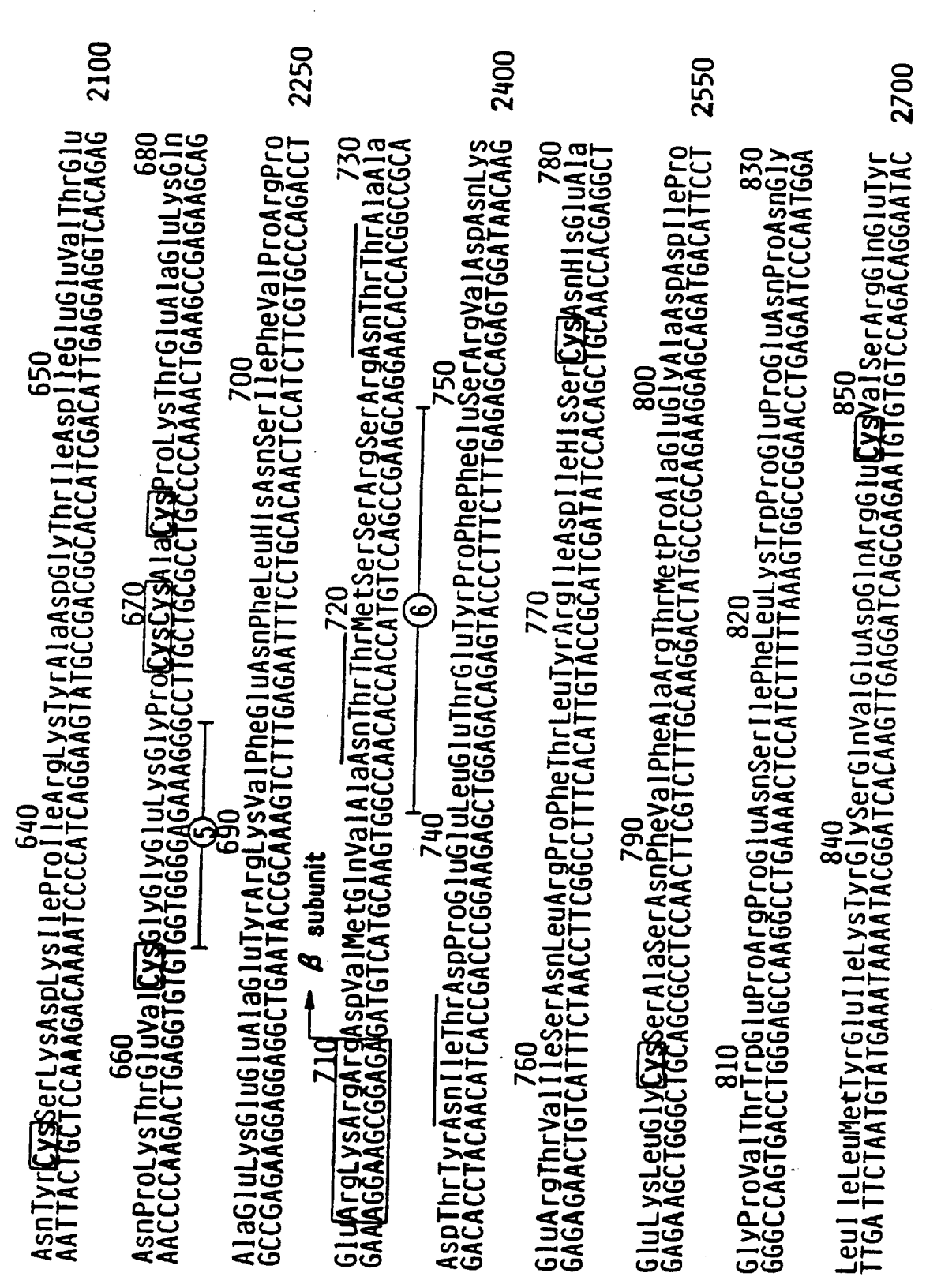

FIGS. 1A–1G provide the amino acid SEQ ID NO:2 and nucleotide SEQ ID NO:1 sequence of IGF-1 receptor. Amino acids −30 to −1 represent the signal peptide sequence.

DETAILED DESCRIPTION OF THE INVENTION

Figure 2:
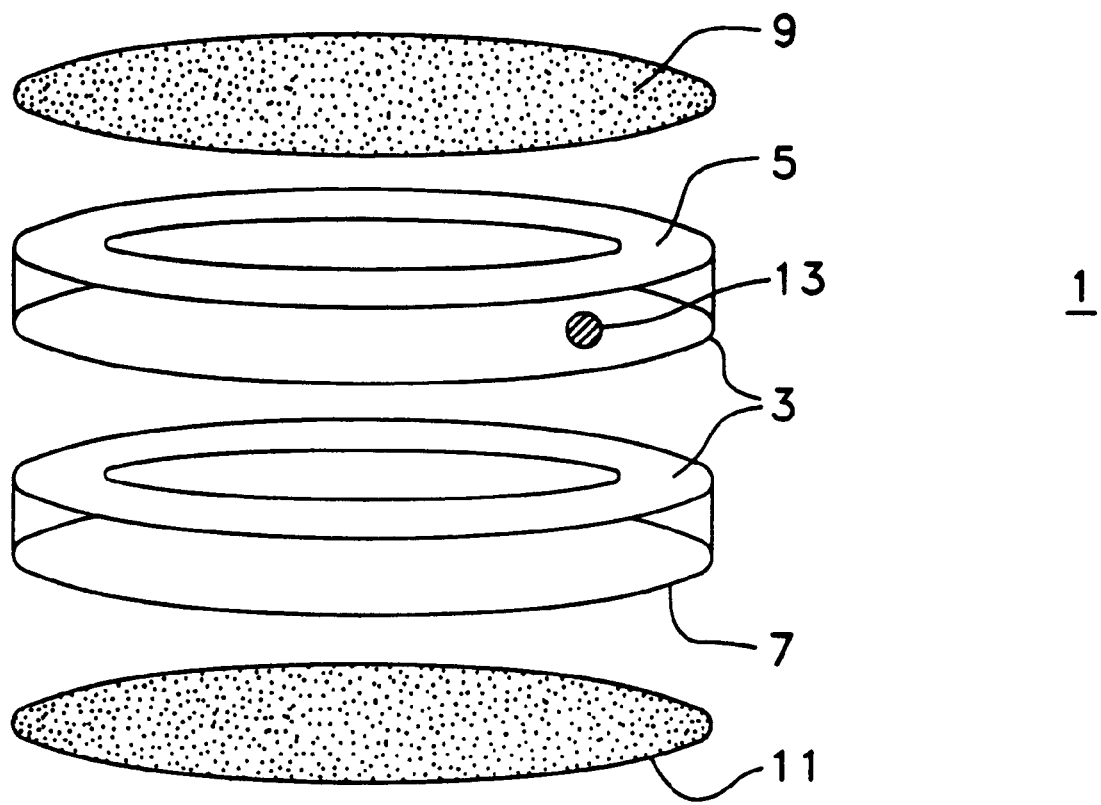
FIG. 2 shows a schematic illustration of a diffusion chamber.

The present invention relates to methods and pharmaceutical compositions comprising soluble IGF-1R for inducing resistance to tumor cells. In preferred embodiments of the invention, individuals having tumors are treated with pharmaceutical compositions comprising gene therapeutic expression vectors, preferably adenovirus or retrovirus, comprising nucleic acid molecules encoding soluble IGF-1R. Such vectors express soluble IGF-1R in tumor cells resulting in reversal of the transformed phenotype, induction of apoptosis, and inhibition of tumorigenesis. In other embodiments of the invention, individuals having tumors are treated by implanting a diffusion chamber comprising tumor cells infected with expression vectors comprising nucleic acid molecules encoding soluble IGF-1R. Alternatively, the diffusion chamber comprises tumor cells cultured with soluble IGF-1R protein. In other embodiments of the invention, individuals having tumors are treated with pharmaceutical compositions comprising soluble IGF-1R protein.

Diseases in which cell elimination by induction of apoptosis include cancer, coronary restinosis after angioplasty, as well as autoimmune diseases. Tumors treatable with the methods of the present invention include and are not limited to melanoma, prostate, ovary, mammary, lungs, and smooth muscle tumors; as well as cells from glioblastoma, bone marrow stem cells, hematopoietic cells, osteoblasts, epithelial cells, fibroblasts. Those having ordinary skill in the art can readily identify individuals who are suspected of suffering from such diseases, conditions and disorders using standard diagnostic techniques.

As used herein, the term "soluble IGF-1R" refers to secreted IGF-1R proteins. Such proteins comprise up to about 800 amino acids of the N-terminus of IGF-1R, such that the C-terminus transmembrane domain is completely deleted or is present to the extent that the protein comprising a portion of the transmembrane domain is not able to be anchored in the cell membrane. Preferably, soluble IGF-1R comprises the N-terminal 486 amino acids without a signal peptide (amino acids 1 to 486 as set forth in FIGS. 1A–1G; SEQ ID NO:5), or comprising 516 amino acids with a signal peptide (amino acids −30 to 486 as set forth in FIGS. 1A–1G; SEQ ID NO:4). In addition, the term "soluble IGF-1R" refers to fragments from about 10 amino acids to about 485 amino acids, such as IGF-1R proteins comprising N-terminal and C-terminal truncations or internal deletions.

In a preferred embodiment of the invention, resistance to tumor cells is induced by treating individuals having tumors with pharmaceutical compositions comprising gene therapeutic expression vectors, preferably adenovirus or retrovirus, comprising nucleic acid molecules encoding soluble IGF-1R. Gene therapeutic expression vectors having nucleic acid molecules encoding soluble IGF-1R serve as gene therapies for individuals to induce apoptosis of tumor cells, and the induction of a host response that kills or inhibits the growth of surviving tumor cells. This method has the following advantages: 1) soluble IGF-1R delivered into tumor cells induces apoptosis; 2) because it is soluble, the infected or transfected cells will produce soluble IGF-1R which will also cause apoptosis of non-transfected cells; and 3) the apoptotic cells induce a host response.

Gene therapy involves the introduction and stable insertion of genetic material into cells. Genetic material can generally be introduced into cells by, for example, transfection or transduction. Nucleic acid molecules encoding soluble IGF-1R are delivered using any one of a variety of transfection or transduction techniques, such as, for example, gene therapeutic expression vectors, i.e., recombinant viral expression vectors, or other suitable delivery means, so as to affect their introduction and expression in compatible host cells.

Transfection refers to introduction of new genetic material into cells by incorporation of added DNA. Transfection can occur by physical or chemical methods. Many transfection techniques are known to those of ordinary skill in the art and include, for example, calcium phosphate DNA co-precipitation, DEAE-dextran DNA transfection, electroporation, and cationic liposome-mediated transfection. In addition, other delivery components are also contemplated such as transferrin-mediated transfection, retrotransposons (see U.S. Ser. No. 5,354,674, incorporated herein by reference), targeted transfection nanoparticles (see U.S. Ser. No. 5,460,831, incorporated herein by reference) and other receptor-mediated means.

Transduction refers to the process of transferring nucleic acid into cells using a DNA or RNA virus. In general, suitable viral vectors include, but are not limited to, DNA viruses such as recombinant adenoviruses, parvoviruses, herpesviruses, poxviruses, adeno-associated viruses and Semliki Forest viruses and recombinant vaccinia viruses or RNA viruses such as recombinant retroviruses. Other recombinant vectors include recombinant prokaryotes which can infect cells and express recombinant genes.

The invention is intended to include such other forms of expression vectors and other suitable delivery means which serve equivalent functions and which become known in the art subsequently hereto.

Cells can be treated in vivo or ex vivo. For ex vivo treatment, cells are isolated from an animal (preferably a human), transformed (i.e., transduced or transfected in vitro) with an expression vector comprising nucleic acid molecules encoding soluble IGF-1R, and then administered to a recipient. Procedures for removing cells from animals are well known to those of ordinary skill in the art. In addition to cells, tissue or the whole or parts of organs may be removed, treated ex vivo and then returned to the patient. Thus, cells, tissue or organs may be cultured, bathed, perfused and the like under conditions for introducing the expression vector encoding soluble IGF-1R into the desired cells. An example of ex vivo gene therapy is set forth in U.S. Ser. No. 5,399,346, incorporated herein by reference.

For in vivo treatment, cells of an animal, preferably a mammal and most preferably a human, are transformed in vivo with an expression vector comprising nucleic acid molecules encoding soluble IGF-1R. The in vivo treatment may involve systemic treatment with a vector such as intravenously, local internal treatment with a vector such as by perfusion, topical treatment with a vector and the like. When performing in vivo therapy, the preferred vectors are based on noncytopathic eukaryotic viruses in which nonessential or complementable genes have been replaced with the gene of interest. Such noncytopathic viruses include retroviruses, the life cycle of which involves reverse transcription of genomic viral RNA into DNA with subsequent proviral integration into host cellular DNA. Retroviruses have recently been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for high-efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, "Gene Transfer and Expression, a Laboratory Manual", W. H. Freeman Co., New York (1990) and Murry, e.d. "Methods in Molecular Biology", Vol. 7, Humana Press, Inc., Cliffton, N.J. (1991).

In preferred embodiments of the present invention, DNA is delivered to competent host cells by means of an adenovirus or parvovirus. One skilled in the art would readily understand this technique of delivering DNA to a host cell by such means. Although the invention preferably includes adenovirus and parvovirus, the invention is intended to include any virus which serves equivalent functions. Viral expression vectors and methods of preparation thereof, such as for example, adenovirus and parvovirus, to transfect or infect host cells are disclosed in U.S. Ser. No. 5,354,678, U.S. Ser. No. 5,173,414, U.S. Ser. No. 5,139,941, and U.S. Ser. No. 5,252,479, all incorporated herein by reference in their entirety. In addition, gene therapeutic expression vectors preferably comprise cell-specific promoters which provide for expression of the linked gene in a cell-specific manner. Thus, in the present invention, a promoter can be chosen which provides for expression of soluble IGF-1R only in the tumor cell to be treated. Standard techniques for the construction of such vectors are well known to those skilled in the art, and can be found in references such as, for example, Sambrook et al., *Molecular Cloning a Laboratory Manual*, Second Ed. Cold Spring Harbor Press (1989), which is incorporated herein by reference.

Alternatively, RNA is delivered to competent host cells by means of a retrovirus. One skilled in the art would readily understand this technique of delivering RNA to a host cell by such means. Any retrovirus which serves to express the protein encoded by the RNA is intended to be included in the present invention.

In preferred embodiments of the present invention, the gene therapeutic expression vector, such as, for example, adenovirus, comprises a nucleic acid molecule encoding soluble human IGF-1 receptor incorporated in such a manner as to allow expression of soluble IGF-1R. A preferred virus for certain applications is the adeno-associated virus, a double-stranded DNA virus. The adeno-associated virus can be engineered to be replication deficient and is capable of infecting a wide range of cell types and species. It further has advantages such as: heat and lipid solvent stability, high transduction frequencies in cells of diverse lineages, including hemopoietic cells; and lack of superinfection inhibition thus allowing multiple series of transductions. Recent reports indicate that the adeno-associated virus can also function in an extrachromosomal fashion. Recombinant genomes that are between 50% and 110% of wild-type adeno-associated virus size can be easily packaged. Thus, a vector such as d13–94 can accommodate an insertion of the size required to encode soluble IGF-1R.

In preferred embodiments, a gene therapeutic expression vector encoding soluble IGF-1R can be constructed by removing all endogenous coding sequences (bases 190–4034) from an infectious molecular clone of an adeno-associated virus (pAV1 from ATCC, Rockville, Md.). The RSV long terminal repeat (LTR) driven soluble IGF-1R and the Neo gene under the control of the SV40 early promoter is then inserted into this virus.

In addition, Semliki Forest virus vectors are useful as transducing agents and include, but are not limited to, pSFV1 and pSFV3-lacZ (Gibco-BRL). These vectors contain a polylinker for insertion of foreign genes therein which is followed by a series of stop codons. The gene of choice is inserted into the polylinker region and viruses are generated using the in vitro packaging helper virus system also provided by Gibco-BRL. Following the directions of the manufacturer and the disclosure contained herein, it is a relatively simple matter for one of skill in the art to generate Semliki Forest virus vectors capable of expressing soluble IGF-1R proteins of the invention.

Preferably, soluble IGF-1R is expressed in a cell-specific manner from a tumor cell-specific promoter. The nucleic acid sequence for introduction into gene therapeutic expression vectors can be derived from, for example, the CVN-IGF-1R plasmid (Ullrich, et al., *EMBO J.*, 1986, 5, 503, incorporated herein in its entirety by reference), which contains the full length coding sequence cDNA of the human IGF-1 receptor (See FIGS. 1A–1G) under the control of the SV40 promoter. The CVN-IGF-1R plasmid may be manipulated by well known techniques to produce additional gene constructs which encode soluble IGF-1R proteins of varying length in amino acids. Such gene constructs may be used to prepare gene therapeutic expression vectors encoding soluble IGF-1R proteins of varying length.

For example, by using a frame shift mutation strategy, Applicants produced IGF-1R cDNA SEQ ID NO:3 that produces a full-length mRNA but a truncated receptor, which is, after cleavage of the signal peptide, 486 amino acids long (SEQ ID NO:5). Alternatively, the soluble receptor can additionally consist of the signal peptide (amino acids −30 to −1 of FIG. 1A), which then provides a soluble IGF-1R protein that is 516 amino acids long (SEQ ID NO:4). In addition, it is contemplated that soluble IGF-1R may comprise up to about 800 amino acids, as long as the transmembrane region of IGF-1R is such that it no longer anchors the receptor in the cell membrane. Additional gene constructs can be prepared by similar techniques to produce soluble IGF-1R proteins having a selected number of amino acids. The truncated receptor is secreted into the medium and can be detected by, for example, immunoprecipitation with antibodies.

Additional gene constructs encoding species of soluble IGF-1R may be constructed as desired. For example, fragments of soluble IGF-1R may be produced which retain the ability to induce apoptosis. Such fragments can be, for example, C-terminal truncations, N-terminal truncations, and proteins comprising internal deletions. The fragments can be as long as 515 amino acids, for proteins comprising the signal peptide, and 485 amino acids for proteins not comprising the signal peptide, and as short as 10 amino acids at the N-terminus, C-terminus, or internal portion of the IGF-1R protein. Such species may be constructed by using techniques such as, for example, site-specific mutagenesis, and similar techniques which are well within the ability of the art skilled. Thus, the present invention also contemplates soluble IGF-1R proteins and gene constructs encoding proteins having portions of the complete IGF-1R sequence. Moreover, conservative amino acid substitutions may be made throughout the protein without significantly reducing apoptosis activity.

Pharmaceutical compositions of the invention comprise gene therapeutic expression vectors having nucleic acid molecules encoding soluble IGF-1R, such as those set forth above. Such nucleic acid molecules induce apoptosis and inhibit tumor growth in individuals who have tumors. Pharmaceutical compositions according to the invention comprise a pharmaceutically acceptable carrier in combination with nucleic acid molecules encoding soluble IGF-1R. Pharmaceutical formulations are well known and pharmaceutical compositions comprising nucleic acid molecules encoding soluble IGF-1R may be routinely formulated by one having ordinary skill in the art. Suitable pharmaceutical carriers are described in *Remington's Pharmaceutical Sciences*, A. Osol, a standard reference text in this field, which is incorporated herein by reference. The present invention relates to an injectable pharmaceutical composition that comprises a pharmaceutically acceptable carrier and nucleic acid molecule encoding soluble IGF-1R. Nucleic acid molecule encoding soluble IGF-1R is preferably sterile and combined with a sterile pharmaceutical carrier.

In some embodiments, for example, nucleic acid molecules encoding soluble IGF-1R can be formulated as a solution, suspension, emulsion or lyophilized powder in association with a pharmaceutically acceptable vehicle. Examples of such vehicles are water, saline, Ringer's solution, dextrose solution, and 5% human serum albumin. Liposomes and nonaqueous vehicles such as fixed oils may also be used. The vehicle or lyophilized powder may contain additives that maintain isotonicity (e.g., sodium chloride, mannitol) and chemical stability (e.g., buffers and preservatives). The formulation is sterilized by commonly used techniques.

An injectable composition may comprise nucleic acid molecules encoding soluble IGF-1R in a diluting agent such as, for example, sterile water, electrolytes/dextrose, fatty oils of vegetable origin, fatty esters, or polyols, such as propylene glycol and polyethylene glycol. The injectable must be sterile and free of pyrogens.

Pharmaceutical compositions according to the invention include delivery components in combination with nucleic acid molecules that encode soluble IGF-1R which further comprise a pharmaceutically acceptable carriers or vehicles, such as, for example, saline. Any medium may be used which allows for successful delivery of the nucleic acid. One skilled in the art would readily comprehend the multitude of pharmaceutically acceptable media that may be used in the present invention.

The pharmaceutical compositions of the present invention may be administered by any means that enables the active agent to reach the agent's site of action in the body of a mammal. Pharmaceutical compositions may be administered parenterally, i.e., intravenous, subcutaneous, intramuscular. Intravenous administration is the preferred route. Alternatively, tumor cells may be removed from an individual, and nucleic acid molecules encoding soluble IGF-1R protein introduced therein in vitro by techniques such as, for example, nake DNA transfection, microinjection, cell fusion, infection with virions, etc.

Dosage varies depending upon known factors such as the pharmacodynamic characteristics of the particular agent, and its mode and route of administration; age, health, and weight of the recipient; nature and extent of symptoms, kind of concurrent treatment, frequency of treatment, and the effect desired.

In another embodiment of the present invention, individuals having tumors can be treated by implanting a diffusion chamber comprising medium and tumor cells infected or transfected with expression vectors comprising a nucleic acid molecule encoding soluble IGF-1R.

Resistance to tumor growth is induced by placing tumor cells supplemented with nucleic acid molecules encoding soluble IGF-1R in a diffusion chamber thereby producing a cell-containing chamber, inserting the cell-containing chamber into a mammal for a therapeutically effective time, thereby inducing resistance to tumor growth. Mammals subsequently subcutaneously challenged with wild-type tumor cells are resistant to the tumor cells. In addition, regression of already established tumors is evidenced. The present invention is also directed to a method of inducing apoptosis. This application is related to U.S. application Ser. No. 08/340,732, filed Nov. 16, 1994, which is incorporated herein in its entirety by reference.

The tumor cells can be transfected with a nucleic Hacid molecule encoding a protein encoding soluble IGF-1R, such as the protein having the amino acid sequence set forth in SEQ ID NO:5, SEQ ID NO:4, or a fragment thereof. The diffusion chamber containing the IGF-1R-infected cells is implanted for a therapeutically effective time. A therapeutically effective time is a time permitting death of the cells in said diffusion chamber and resistance of tumor growth in the mammal. The soluble IGF-1R produced by the tumor cells causes the death of the tumor cells in the chamber and elicits a host response such that the cell death has a growth inhibiting effect, i.e., a resistant effect, on a tumor or tumors in the mammal in which the chamber is placed. Tumors which are treatable with the methods of the present invention may be primary or secondary, benign, malignant, metastatic, or micrometastatic tumors.

Therapeutically effective doses of nucleic acid molecules encoding soluble IGF-1R will be about that amount of nucleic acid alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable.

Tumorous tissue may be placed in culture together with nucleic acid molecules encoding soluble IGF-1R. Tumorous tissue may be excised from the patient in which the diffusion chamber will be inserted, however, tumorous tissue from another source, and/or that which has been cultured in vitro, may also be used together with nucleic acid molecules encoding soluble IGF-1R. The tumor cells are cultured for a therapeutically effective amount of time such that apoptosis of these cells is induced thereby causing resistance to tumor growth.

Before placing the cell-containing diffusion chamber into a mammal, cells may be gently dissociated with trypsin, incubated with nucleic acid molecules encoding soluble IGF-1R, and placed in the chamber. The chamber may then be implanted. Accordingly, any adverse treatments to the cells are performed in vitro thereby eliminating adversity to the host mammal. In addition, cells may be placed into a chamber and the chamber directly implanted into a mammal.

The present invention employs the use of a diffusion chamber, in which the cells are contained. Cells are impermeable to a filter fitted on the diffusion chamber; they cannot leave or enter the chamber. The filter on the diffusion chamber has pores in the size range of about 0.25 $\mu$m or smaller, preferably about 0.1 $\mu$m in diameter. Lange, et al., *J. Immunol.*, 1994, 153, 205; and Lanza, et al., *Transplantation*, 1994, 57, 1371, both incorporated herein by reference in their entirety. Accordingly, cell death or apoptosis, can be quantitatively determined. The use of a diffusion chamber can be extended to other cell lines, even non-syngeneic, and even from different species, because of the rapidity with which cell death occurs, about 24 hours, well before any immune reaction could be established. Indeed, 3 types of cells with an intact number of IGF-1Rs (human melanoma, rat rhabdomyosarcoma and murine p6 cells), double in number in 24 hours, regardless of whether they are syngeneic or not, while cells with decreased number of IGF-1Rs, die.

Diffusion chambers useful in the present invention include any chamber which does not allow passage of cells between the chamber and the mammal in which it is implanted, however, permits interchange and passage of factors between the chamber and the mammal. The chamber may allow for multiple and sequential sampling of the contents, without contamination and without sacrificing the mammal, therefore significantly reducing the number of implantation procedures performed on the mammal.

Referring to FIG. 2, the diffusion chamber (1) may have a chamber barrel (3) having two ends, a first end (5) and a second end (7). The barrel may be comprised of one or more rings secured together by non-toxic means. The chamber is fitted at each end with a filter, a first filter (9) and a second filter (11). The filters are porous to factors such that the factors may pass between the chamber and the mammal. The filter pores size may be about 0.25 $\mu$m or smaller, preferably about 0.1 $\mu$m. The filters may be made of plastic, teflon, polyester, or any inert material which is strong, flexible and able to withstand chemical treatments. The filters may be secured in position with rubber gaskets which may also provide a tighter seal. On the barrel portion of the chamber, an opening (13) is provided which may be covered by a cap which is accessed from outside of the mammal's body once the chamber is implanted. The cap may be screw on type of self sealing rubber and fitted to the opening. Sampling of the chamber contents may thus be performed by accessing the opening by removing the cap on the outside of the mammal's body and inserting an ordinary needle and syringe. The chamber may be made of any substance, such as and not limited to plastic, teflon, lucite, titanium, or any inert material, which is non-toxic to, and well tolerated by, mammals. In addition, the chambers should be able to survive sterilization.

The chamber may be implanted in the following non-limiting ways: subcutaneously or intraperitoneally, for example. The chamber may be removed about 24 to about 30 hours after implantation. Alternatively, a refillable chamber may be employed such that the chamber may be re-used for treatments and emptied following treatments.

Tumor cells used in the diffusion chambers of the present invention include and are not limited to autografts, allografts, syngeneic, non-syngeneic and xenografts. Cells which may be cultured in a medium supplemented with nucleic acid molecules encoding soluble IGF-1R in a diffusion chamber include any type of cell which upon apoptosis induces resistance to tumor growth, including and not limited to tumor cells. Preferably, tumor cells are placed in a diffusion chamber which is implanted in a mammal, wherein the tumor cells may preferably be the same type of tumor to which resistance is induced. However, an embodiment of the present invention includes tumors cultured in a diffusion chamber which are of a different type than the tumor to which resistance is granted. In addition, any type of cell which undergoes apoptosis and induces resistance to tumor growth is useful in the present invention.

In another embodiment of the present invention, individuals having tumors are treated by implanting a diffusion chamber comprising tumor cells in medium supplemented with soluble IGF-1R protein, or a fragment thereof, in a manner similar to that described above for nucleic acid molecules encoding soluble IGF-1R. The soluble IGF-1R which supplements the tumor cell culture in the diffusion chamber may be selected from any species of soluble IGF-1R, such as and not limited to, a protein having the amino acid sequence set forth in SEQ ID NO:5, SEQ ID NO:4, or a fragment thereof.

The tumor cells can be treated with soluble IGF-1R, such as the protein having the amino acid sequence set forth in SEQ ID NO:5, SEQ ID NO:4, or a fragment thereof. The diffusion chamber containing the IGF-1R-treated cells is implanted for a therapeutically effective time, as set forth above. Therapeutically effective doses of soluble IGF-1R will be about that amount of soluble IGF-1R alone; dosages will be set with regard to weight, and clinical condition of the patient. The proportional ratio of active ingredient to culture medium will naturally depend on the chemical nature, solubility, and stability of the compounds, as well as the dosage contemplated. The culture medium is also pharmaceutically acceptable.

In another embodiment of the present invention, individuals having tumors are treated with pharmaceutical compositions comprising soluble IGF-1R protein. Soluble IGF-1R preferably comprises the amino acid sequence set forth in SEQ ID NO:5 or SEQ ID NO:4. Soluble IGF-1R can be administered as a pharmaceutical composition, such as those described above for nucleic acid molecules encoding IGF-1R, to a mammal topically, intradermally, intravenously, intramuscularly, intraperitoneally, subcutaneously, and intraosseously.

The present invention provides substantially purified soluble IGF-1R which has the amino acid sequence set forth in SEQ ID NO:5, or SEQ ID NO:4 or fragments thereof.

Soluble IGF-1R can be produced by recombinant DNA methods or synthesized by standard protein synthesis techniques.

Soluble IGF-1R proteins of the present invention can be prepared using recombinant DNA methods to produce a gene construct comprising a nucleic acid molecule encoding soluble IGF-1R protein, or portions thereof, including initiation and termination signals operably linked to regulatory elements including a promoter and polyadenylation signals capable of directing expression in host cells. The regulatory elements of the gene constructs of the invention are capable of directing expression in mammalian cells, specifically human cells. The regulatory elements include a promoter and a polyadenylation signal. In addition, other elements, such as a Kozak region, may also be included in the gene construct.

The gene construct is inserted into an appropriate vector, i.e., an expression plasmid, cosmid or YAC vector. Promoters and polyadenylation signals used must be functional within the host cells. In order to maximize protein production, regulatory sequences may be selected which are well suited for gene expression in the cells into which the construct is administered. Moreover, codons may be selected which are most efficiently transcribed in the cell. One having ordinary skill in the art can produce DNA constructs which are functional in host cells.

Examples of promoters useful to practice the present invention include but are not limited to promoters from Simian Virus 40 (SV40), Mouse Mammary Tumor Virus (MMTV) promoter, Human Immunodeficiency Virus (HIV) such as the Long Terminal Repeat (LTR) promoter, Maloney Virus, ALV, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine and human metalothionein.

Examples of polyadenylation signals useful to practice the present invention include but are not limited to SV4 polyadenylation signals and LTR polyadenylation signals. In particular, the SV4 polyadenylation signal which is in pCEP4 plasmid (Invitrogen, San Diego, Calif.), referred to as the SV40 polyadenylation signal, can be used.

One having ordinary skill in the art can obtain a nucleic acid molecule that encodes soluble IGF-1R and insert it into an expression vector using standard techniques and readily available starting materials. The present invention relates to a recombinant expression vector that comprises a nucleic acid molecule having a nucleotide sequence that encodes soluble IGF-1R. As used, herein, the term "recombinant expression vector" is meant to refer to a plasmid, phage, viral particle or other vector which, when introduced into an appropriate host cell, contains the necessary genetic elements to direct expression of the coding sequence that encodes the soluble IGF-1R of the invention. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform or transfect host cells and facilitate expression of coding sequences. The recombinant expression vectors of the invention are useful for transforming or transfecting host cells to prepare recombinant expression systems for preparing soluble IGF-1R of the invention.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of proteins in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as CHO cells. One having ordinary skill in the art can use these commercial expression vectors and systems or others to produce soluble IGF-1R of the invention using routine techniques and readily available starting materials. See e.g., Sambrook et al., *Molecular Cloning a Laboratory Manual*, Second Ed. Cold Spring Harbor Press (1989) which is incorporated herein by reference. Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989). Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions. The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes soluble IGF-1R is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate soluble IGF-1R that is produced using such expression systems. The methods of purifying soluble IGF-1R include using antibodies which specifically bind to soluble IGF-1R in immunoaffinity methodology.

Examples of genetic constructs include soluble IGF-1R operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes soluble IGF-1R from readily available starting materials.

In addition to producing these proteins by recombinant techniques, automated peptide synthesizers may also be employed to produce soluble IGF-1R of the invention. Such techniques are well known to those having ordinary skill in the art and are useful if derivatives which have substitutions not provided for in DNA-encoded protein production.

The present invention relates to host cells that comprise the recombinant expression vector that includes a nucleic acid molecule having a nucleotide sequence that encodes soluble IGF-1R. Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic non-human mammal that comprises the recombinant expression vector that comprises a nucleic acid sequence that encodes soluble IGF-1R. Transgenic non-human mammals useful to produce recombinant proteins are well known as are the expression vectors necessary and the techniques for generating transgenic animals. Generally, the transgenic animal comprises a recombinant expression vector in which the nucleotide sequence that encodes soluble IGF-1R of the invention is operably linked to a mammary cell specific promoter whereby the coding sequence is only expressed in mammary cells and the recombinant protein so expressed is recovered from the animal's milk.

In some embodiments of the invention, transgenic non-human animals are generated. The transgenic animals according to the invention contain nucleotide sequences that encode soluble IGF-1R under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce soluble IGF-1R. Preferred animals are rodents, particularly rats and mice, and goats.

The present invention underscores the massive apoptosis in vivo induced by transfected or transduced soluble IGF-1R, which makes it a good candidate for inhibition of tumorigenesis and tumor regression in human patients. Treatment with soluble IGF-1R not only induces apoptosis of tumor cells, but also induces a host response that kills tumor cells not expressing soluble IGF-1R. Thus, delivery of soluble IGF-1R into tumor cells would kill the cells that have taken up the vector carrying it and this would start a secondary response that kills the surviving tumor cells. This double-edged sword would make this approach very effective. It is effective in animals, where it induces apoptosis and elicits a host response, with little effect on normal cells. Because it is secreted, soluble IGF-1R will affect surrounding cells, and therefore increase its effectiveness. The application of soluble IGF-1R intends to cover all uses against various types of tumor cells, regardless of delivery route, whether they are primary tumors, residual tumors or metastases.

For purposes of the present invention, mammals include and are not limited to the Order Rodentia, such as mice; Order Logomorpha, such as rabbits; more particularly the Order Carnivora, including Felines (cats) and Canines (dogs); even more particularly the Order Artiodactyla, Bovines (cows) and Suines (pigs); and the Order Perissodactyla, including Equines (horses); and most particularly the Order Primates, Ceboids and Simoids (monkeys) and Anthropoids (humans and apes). The mammals of most preferred embodiments are humans.

The following examples are illustrative but are not meant to be limiting of the invention.

EXAMPLES

Example 1

Construction of Soluble IGF-1R Plasmid

A soluble IGF-1R protein truncated at amino acid residue 486 was prepared by the following method. Methods for the production and activity of soluble IGF-1R are also disclosed in D'Ambrosio, et al., *Cancer Res.*, 1996, 56, 4013, incorporated in its entirety herein by reference. The CVN-IGF-1R plasmid (Ullrich, et al., *EMBO J.*, 1986, 5, 503, incorporated herein in its entirety by reference), containing the full length coding sequence cDNA of the human IGF-1 receptor, under the control of the SV40 promoter, was digested with AgeI, which cuts at nucleotide 1574 (numbering according to Ullrich, et al., *EMBO J.*, 1986, 5, 503). The overhangs were filled with Klenow and the plasmid was religated. This procedure generates a frame shift mutation that results in the creation of an early stop codon 12 nucleotides downstream from the AgeI site. The mutation was confirmed by sequencing both strands (not shown). The wild type and mutant DNA sequences, and their translation, in the area corresponding to the mutation are shown below. The AgeI site is underlined. The mutation abrogates this restriction site.

```
Wild type                                             (SEQ ID NO:1)
. . . TGG CAC CGG TAC CGG CCC CCT GAC TAC . . .

. . . W   H   R   Y   R   P   P   D   Y . . .

Mutant                                                (SEQ ID NO:3)
. . . TGG CAC CGG CCG GTA CCG GCC CCC TGA CTAC . . .

. . . W   H   R   P   V   P   A   P   *
```

WHR are amino acids 509–511, if the signal peptide is included (479–481 without the signal peptide). The soluble receptor is, therefore, 516 amino acids long (SEQ ID NO:4) or 486 (SEQ ID NO:5) without the signal peptide. The expression plasmid containing the nucleic acid sequence encoding soluble IGF-1R, and containing the neo-resistance gene, is designated pIGFIRsol. Additional soluble IGF-1R proteins truncated at other positions can be constructed using similar techniques.

Example 2

Preparation of pGEX Fusion Protein

Soluble IGF-1R can be expressed as a fusion protein. The pGEX-5x-3/IGFIRsol, a plasmid encoding the IGF-1R soluble protein, was prepared as follows. A PCR fragment corresponding to the soluble receptor (without the signal peptide) was created using mutagenic primers. The 5' primer GGATCCTAGAAATCTGCGGGCCAGGC, SEQ ID NO:6, contains an artificial BamHI site followed by the cDNA sequence, starting at nucleotide 135 and ending at nucleotide 153. The 3' reverse primer TCAGGGGGCCGGTACCGGCC, SEQ ID NO:7, contains two mismatches compared to the original cDNA sequence, resulting in a disruption of the AgeI restriction site. After sequencing on both strands, the PCR fragment was subcloned in the EcoRI site of the PCRII vector (InVitrogen), amplified and digested with BamHI and EcoRI.

pGEX-5x-3/IGFIRsol was constructed by digesting PGEX-5x-3 with BamHI-EcoRI and ligating the BamHI-EcoRI IGFIRsol fragment. Five colonies of BL21(DE3) transformed bacteria were selected, stimulated with 0.1 mM IPTG and checked for the GST fusion protein levels by SDS-PAGE and Coomassie blue staining. One colony expressing the highest level of GST fusion protein was chosen for large scale amplification. The GST fusion protein was then purified according to the protocol suggested by GST purification modules manufacturer (Pharmacia).

Example 3

Immunoprecipitation of Soluble IGF-1R

The GST/IGFIRsol protein was immunoprecipitated overnight with anti-GST polyclonal antibody (Santa Cruz Lab) and Protein-A Agarose anti-mouse Ig (Oncogene Science). Alternatively, soluble IGF-1R may be immunoprecipitated with antibodies to IGF-1R (a domain of the IGF-1R; cat# sc-712; Santa Cruz Lab). These antibodies may be stained with anti-rabbit IgG peroxidase conjugated antibody (Oncogene Science) and detected with an ECL system (Amersham).

Antibodies to soluble IGF-1R are preferably monoclonal antibodies, which are commercially available. The antibodies are preferably raised against soluble IGF-1R protein made in human cells. Immunoassays are well known and there design may be routinely undertaken by those having ordinary skill in the art. Those having ordinary skill in the art can produce monoclonal antibodies which specifically bind to soluble IGF-1R protein using standard techniques and readily available starting materials. The techniques for producing monoclonal antibodies are outlined in Harlow, E. and D. Lane, (1988) ANTIBODIES: A Laboratory Manual, Cold Spring Harbor Laboratory, Cold Spring Harbor N.Y., which is incorporated herein by reference, provide detailed guidance for the production of hybridomas and monoclonal antibodies which specifically bind to target proteins. It is within the scope of the present invention to include FAbs and F(Ab)$_2$s which specifically bind to soluble IGF-1R protein in place of antibodies.

Briefly, the soluble IGF-1R protein is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the soluble IGF-1R protein, the hybridoma which produces them is cultured to produce a continuous supply of anti-soluble IGF-1R protein specific antibodies.

Example 4

Preparation of Tumor Cell Lines

The C6 rat glioblastoma cell line was used in several experiments. The C6 cell line is syngeneic in BD-IX rats (Charles River Breeders Laboratories, Boston, Mass.). This cell line has been described in detail by Trojan, et al., Science, 1993, 259, 94; Resnicoff, et al., Cancer Res., 1994, 54, 2218; Resnicoff, et al., Cancer Res., 1994, 54, 4848; and Trojan, et al., Proc. Natl. Acad. Sci. U.S.A., 1992, 89, 4874, the disclosures of which are hereby incorporated by reference in their entirety. Other cell lines used were a human melanoma cell line, FO-1, and a rat rhabdomyosarcoma cell line, BA 1112. Martin, et al., Eur. J. Cancer Clin. Oncol., 1983, 19, 791, incorporated herein by reference in its entirety. The cells were pre-incubated at 39° C. for 24 hours, before inoculation in the diffusion chambers.

Cells were passaged in RPMI 1640 supplemented with 5% calf serum and 5% fetal bovine serum. $8 \times 10^4$ cells were plated in 35 mm dishes in 10% serum; after 12 hours, the growth medium was removed and replaced with serum-free medium supplemented with 0.1% bovine serum albumin (fraction V) and 1.0 $\mu$M ferrous sulfate, with or without IGF-1 (10 ng/ml), as disclosed by Resnicoff, et al., Cancer Res., 1994, 5, 2218, incorporated herein by reference in its entirety.

Balb/c 3T3 are 3T3 cells, passaged for several years, and p6 cells are Balb/c 3T3 cells stably transfected with, and overexpressing a human IGF-1R cDNA. Pietrzkowski, et al., Cell Growth & Diff., 1992, 3, 199, incorporated herein by reference in its entirety. (tsA)R$^-$ and (tsA)R$^+$ cells have been described by Sell, et al., Proc. Natl. Acad. Sci. U.S.A., 1993, 90, 11217. (tsa)R$^-$ cells have no IGF-1 receptors, while (tsa)R+ overexpresses a human IGF-1R cDNA. Both (tsa)R− and (tsa)R+ express SV40 T antigen.

To establish C6 cells expressing IGFIRsol, C6 cells were co-transfected with the IGFIRsol plasmid and pPDV6+ plasmid, containing the puromycin resistance gene. DeAngelis, et al., *J. Cell. Physiol.,* 1995, 164, 214, incorporated herein in its entirety. Cells were selected in 2.5 mg/ml of puromycin; the resulting clones were switched to medium containing 1,400 mg/ml of G418 to keep them under strict selection (the pIGFIRsol plasmid contains the neo-resistance gene). Balb/IGFIRsol were obtained by stable transfection with the IGFIRsol plasmid and subsequent selection in 1,400 mg/ml of G418. R− cells were co-transfected with the pIGFIRsol plasmid and pdeltaSUpac (also containing the puromycin resistance gene), and the cells were selected in 2.5 μg/ml of puromycin.

Example 5

Diffusion Chamber

Diffusion chambers were constructed from 14 mm Lucite rings with 0.1 μm pore-sized hydrophilic Durapore membranes (Millipore, Bedford, Mass.). The diffusion chambers were sterilized with ethylene oxide prior to use. After the cells were pre-incubated for 24 hours according to the methods of Resnicoff, et al., *Cancer Res.,* 1994, 54, 2218, incorporated herein by reference in its entirety, and as set forth above, they were placed into the chambers, which were then inserted into the subcutaneous tissue of rats, under anesthesia with Halothane (inhalant).

Aliquots of $5 \times 10^5$ cells were placed in diffusion chambers, that were then inserted in the subcutaneous tissue of syngeneic rats, and removed at various intervals thereafter. The number of cells in each chamber were counted, also the percentage of cells stained by trypan blue, and finally, the residual cells were plated in tissue culture dishes. Cell death occurs so rapidly and because cells in a diffusion chamber are, at least in part, protected from an immune response. Lanza, et al., *Transplantation,* 1994, 57, 1371. Cell recovery is the real measure of growth and survival, since viability of the recovered cells (as determined by trypan blue) was close to 100%.

Example 6

Growth Curves

Two different types of experiments were performed on C6 and C6/IGFIRsol cells. First, C6 and C6/IGFIRsol cells were seeded at the density of $3 \times 10^4$ cells/35 mm dishes and switched to SFM or SFM+IGF-1 (20 ng/ml) after 24 hours. Second, C6 cells were seeded at the density of $8 \times 10^4$ cells/35 mm dishes and switched after 24 hours to conditioned medium from C6 or C6/IGFIRsol cells.

Conditioned medium from R−/IGFIRsol and Balb/IGFIRsol sells was tested on p6 cell growth. p6 cells were plated at a density of $3 \times 10^4$ cells/35 mm dishes in DMEM containing 10% FBS. After 24 hours, the cells were washed with Hank's solution and growing medium was replaced with conditioned medium from different R−/IGFIRsol or Balb/IGFIRsol clones and parental cell lines, alone or with IGF-1 (20 ng/ml). p6 in SFM or SFM+IGF-1 (20 ng/ml) were used as a control.

In every experiment, the growth response was determined after 96 hours of culture, by harvesting and counting the cells in a hemocytometer. All experiments were done in triplicate.

Example 7

Determination of Apoptosis

Briefly, a diffusion chamber was implanted into the subcutaneous tissue of rats or mice. The diffusion chamber, as disclosed in Abraham, et al., *J. Parasitol.,* 1993, 79, 571, contains tumor cells supplemented with soluble IGF-1R, as a protein or expressed from an expression vector as described above. The tumor cells in the diffusion chamber behave essentially as cells injected into the subcutaneousl tissue of animals. The diffusion chamber was removed after a period of time and the cells removed.

Cells were lysed in 50 μl of lysis buffer (10 mM EDTA, 50 mM Tris pH 8,0.5% sodium dodecyl sulfate, 0.5 mg/ml proteinase K). RNAse A (0.5 mg/ml) was added and lysates were incubated for 1 hour at 37° C. Two phenol extraction (equal volumes) were performed, followed by one chloroform extraction. DNA was precipitated with two volumes of ice-cold ethanol and incubated at −80° C. for 1 hour. DNA was pelleted by centrifugation at 14,000 rpm for 10 minutes at 4° C. Pellets were air-dried for 30 minutes, resuspended in 50 μl of Tris-EDTA pH 8. DNA was electrophoresed in a 1.8% agarose gel in 1× TBE running buffer (0.05 M Tris base, 0.05 M boric acid, 1 mM disodium EDTA), according to the methods of Preston, et al., *Cancer Res.,* 1994, 54, 4214, incorporated herein by reference in its entirety.

Example 8

Tumorigenesis

To determine the ability of C6 cells and derivative lines to produce tumors, syngeneic BD IX rats (Charles River Breeders Laboratories, Boston, Mass.) were injected subcutaneously with $10^7$ cells, as described in Resnicoff, et al., incorporated herein by reference (*Cancer Res.,* 1994, 54, 2218). Wild type C6 cell sat this concentration give palpable tumors in 4 days, and the animals usually die or have to be killed after 20–25 days. Rats that did not develop tumors were kept under observation for as long as 62 days. The rats used in the diffusion chamber experiments were then used to determine the host response that is induced in rats by cells with decreased numbers of IGF-1Rs, as set forth in Resnicoff, et al., *Cancer Res.,* 1994, 54, 2218.

Example 9

Generating Cell Lines Expressing Soluble IGF-1R

R− cells were co-transfected with the pIGFIRsol and pdeltaSUpac (containing the puromycin resistance gene), and the cells were selected in 2.5 μg/ml of puromycin. Zhou-Li, et al., *Mol. Cell. Biol.,* 1995, 15, 4232, incorporated herein by reference. After selection and screening, several clones were obtained from three different original cell lines: Balb/c 3T3, R− cells and C6 rat glioblastoma cells. The Balb/c 3T3 and R− derived clones were used largely to prepare conditioned medium to be tested on other cell types. C6 cells, wild type or stably transfected with plasmid pIGFIRsol were used as such.

Figure 3:
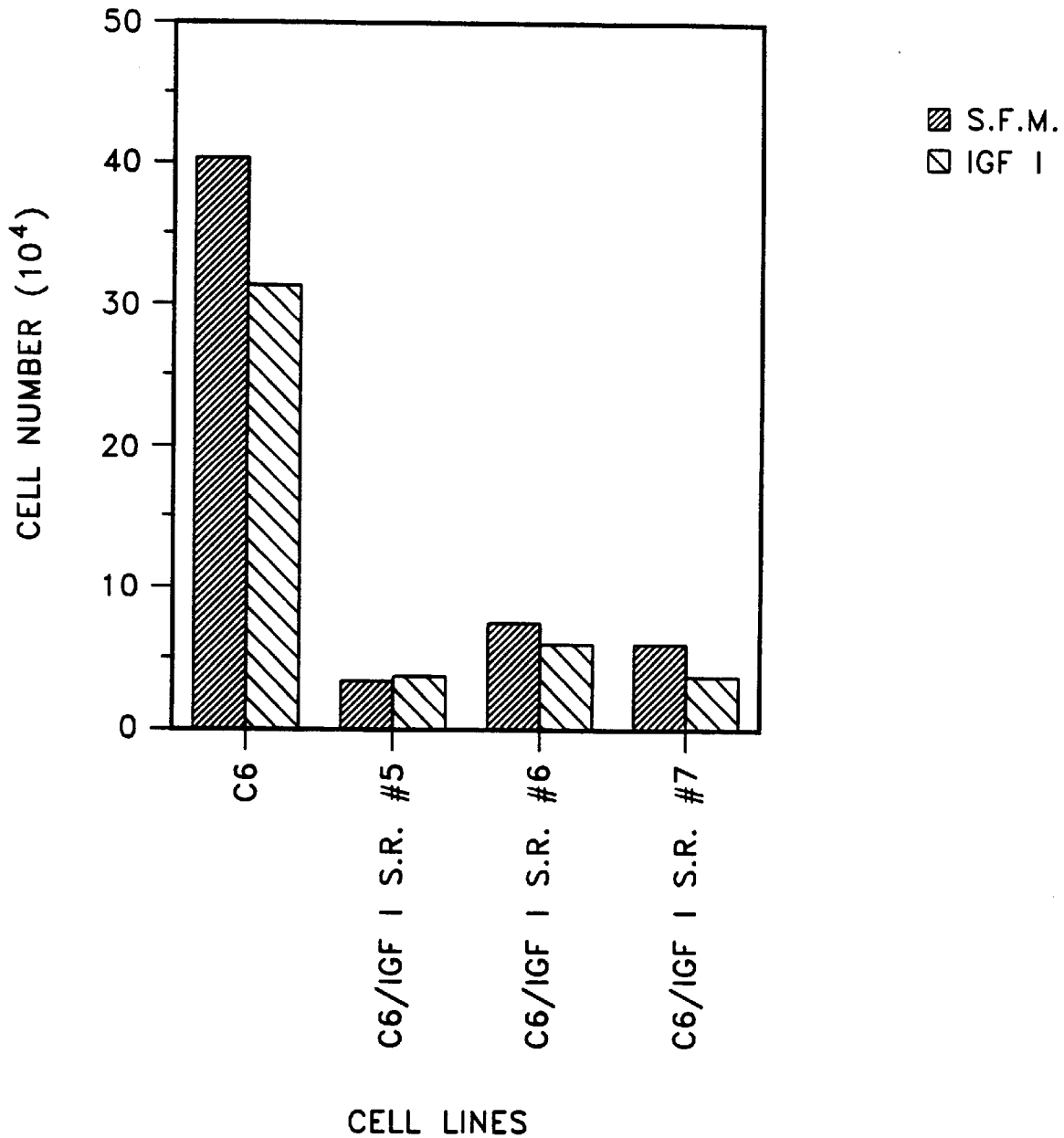
FIG. 3 shows a graph of the growth of C6 cells and derived clones expressing soluble IGF-1R.

Several clones of C6 rat glioblastoma cells stably transfected with plasmid pIGFIRsol were selected and screened. Most of these clones grew significantly more slowly in 10% serum (not shown), and these clones were then tested for the ability to grow in SFM with or without IGF-1 (20 ng/ml). The results of a representative experiment are shown in FIG. 3. C6 cells at 37° C. grow quite well in SFM, even without the addition of IGF-1. Resnicoff, et al., *Cancer Res.,* 1995, 55, 2463. Clones 5, 6 and 7 (all expressing the soluble IGF-1R having 486 amino acids) were markedly inhibited under the same conditions, roughly an 80% inhibition. These and other clones were then tested for the ability to form colonies in soft agar. Wild type C6 cells form colonies in soft agar (Resnicoff, et al., *Cancer Res.*, 1994, 54, 4848), but, with the sole exception of clone 1, all the clones expressing the soluble receptor were markedly impaired in their anchorage independence (Table 1). Inhibition ranged from 46 to 60 percent. This is quite remarkable, because C6 cells have abundant IGF-1 receptors, and produce also some IGF-1. When wild type C6 cells are seeded with the addition of their own conditioned medium, the number of colonies more than doubles.

TABLE 1

Anchorage-independent Growth of C6 Rat Glioblastoma Cells Expressing Soluble IGF-1R

| cell line | number of colonies in soft agar |
|---|---|
| C6 | 301, 317 |
| C6 plus conditioned medium from wt C6 | >1,000 |
| C6/SR clone 1 | 417 |
| clone 4 | 136 |
| clone 5 | 167, 148 |
| clone 6 | 100 |
| clone 7 | 129, 122 |

C6 cells, wild type or stably transfected with plasmid pIGFIRsol, were seeded in soft agar at a density of 5×10³. Colonies >125 μm in diameter were scored after 2 weeks.

Example 10

Soft Agar Assay

C6 and C6/IGFIRsol cells were seeded at 5×10³ cells/35 mm plate in DMEM containing 10% FBS and 0.2% agarose (with 0.4% agarose underlay). C6 cells were also plated at the same density in conditioned medium from C6 or C6/IGFIRsol clones with 10% FBS and 0.2% agarose. Colonies larger than 125 μm were scored after 2 and 1 week, respectively. p6 or T/W cells were plated at the density of 1×10³ cells/35 mm plate in conditioned medium from R⁻/IGFIRsol or Balb/IGFIRsol cells, with 10% FBS and 0.2% agarose (with 0.4% agarose underlay). Colonies larger than 125 μm in diameter were scored after 2 (p6) or 3 (T.W) weeks.

Example 11

Effects of Expression of Soluble IGF-1R

The effects of expression of the soluble IGF-1R on apoptosis of C6 cells placed in the diffusion chamber were determined next. The results are summarized in Table 2.

TABLE 2

C6 Rat Glioblastoma Cells Expressing Soluble IGF-1R Undergo Apoptosis In Vivo

| cell line | percent recovery |
|---|---|
| wild type | 215% |
| clone 4 | 4% |
| clone 6 | 8% |

TABLE 2-continued

C6 Rat Glioblastoma Cells Expressing Soluble IGF-1R Undergo Apoptosis In Vivo

| cell line | percent recovery |
|---|---|
| clone 5 | 0.1% |
| clone 7 | 2% |

Apoptosis was determined in vivo as described in Resnicoff, et al., *Cancer Res.*, 1995, 55, 2463 and in Example 7. In each case, 5×10⁵ cells were inoculated into the diffusion chamber, which was then inserted into the subcutaneous tissue of BD IX rats. Cell numbers were determined after 24 hours and are expressed as percentage of cells originally inoculated.

As usual, wild type C6 cells grow very well in the diffusion chamber, more than doubling their number after 24 hours in vivo. Four clones of C6 cells expressing the soluble receptor were also tested in the diffusion chamber. All of them underwent apoptosis, the recovery of cells ranging from 0.1 to 8 percent. In short, C6 cells expressing the soluble receptor behave like C6 cells expressing an antisense RNA to the IGF-1R RNA (Resnicoff, et al., *Cancer Res.*, 1994, 54, 2218; Resnicoff, et al., *Cancer Res.*, 1994, 54, 4848; and Resnicoff, et al., *Cancer Res.*, 1995, 55, 2463), i.e., they are growth inhibited in monolayers, and in soft agar, and undergo apoptosis in vivo.

Example 12

C6 Cells Expressing Soluble IGF-1R Are No Longer Tumorigenic

Four clones of C6 cells expressing the soluble IGF-1R were injected subcutaneously into BD IX rats (three animals per clone) and none of them developed tumors, while control animals, injected with wild type C6 cells, promptly developed tumors that brought about the death of the animals in 20–25 days (Table 3). The animals injected with the C6 cells expressing the soluble IGF-1R protein having 486 amino acids remained free of tumors for more than three months. To test for the immune response, the animals of Table 2 (who were implanted with diffusion chambers loaded with either wild type C6 cells or with C6 cells expressing the soluble receptor) were used. All animals were tumor-free (since the chambers had been removed to count the surviving cells), and they were challenged two weeks later with wild type C6 cells. Of the animals implanted with chambers containing the C6/SolRec cells, which express soluble IGF-1R, none developed tumors when challenged with wild type C6 cells. Rats implanted with diffusion chambers containing wild type C6 cells developed fatal tumors after subcutaneous injection with wild type C6 cells (Table 3).

TABLE 3

Expression of Soluble IGF-1R Abrogates Tumorigenesis

| cell type injected | challenge | tumors/no. of animals |
|---|---|---|
| wild type | none | 12/12 |
| soluble IGF-1R | none | 0/12 |
| wild type | wild type | 14/14 |
| soluble IGF-1R | wild type | 0/12 |

BD IX rats were injected subcutaneously with either wild type C6 cells or C6 cells expressing soluble IGF-1R. The latter animals have been kept for 90 days without the appearance of tumors. In the second half of the experiment, rats which were implanted for 24 hours with a diffusion chamber containing either wild type C6 cells or C6 cells expressing the soluble IGF-1R. Nine days after removal of the diffusion chamber, the rats were challenged with $10^7$ wild type C6 cells.

The results set forth in Table 3 can be compared to results achieved by antisense therapy. Although antisense oligonucleotides inhibited tumorigenesis in nude mice, eventually all the animals developed tumors, even at the highest concentrations of oligonucleotide (Resnicoff, et al., *Cancer Res.*, 1995, 55, 3739). In contrast, when soluble IGF-1R was used, none of the animals developed tumors (Table 3 above and Table 3 of D'Ambrosio, et al., *Cancer Res.*, 1996, 56, 4013). One rationale for the higher effectiveness of the soluble IGF-1R is that it is secreted into the environment and can therefore act on neighboring cells, even those that do not carry it. The uniqueness of this receptor, coupled with the lack of toxicity on normal cells, offers a higher therapeutic index (Baserga, *Trends in Biotech.*, 1996, 14, 150, incorporated herein by reference).

Example 13

Effect of Conditioned Medium from Cells

Figure 4:
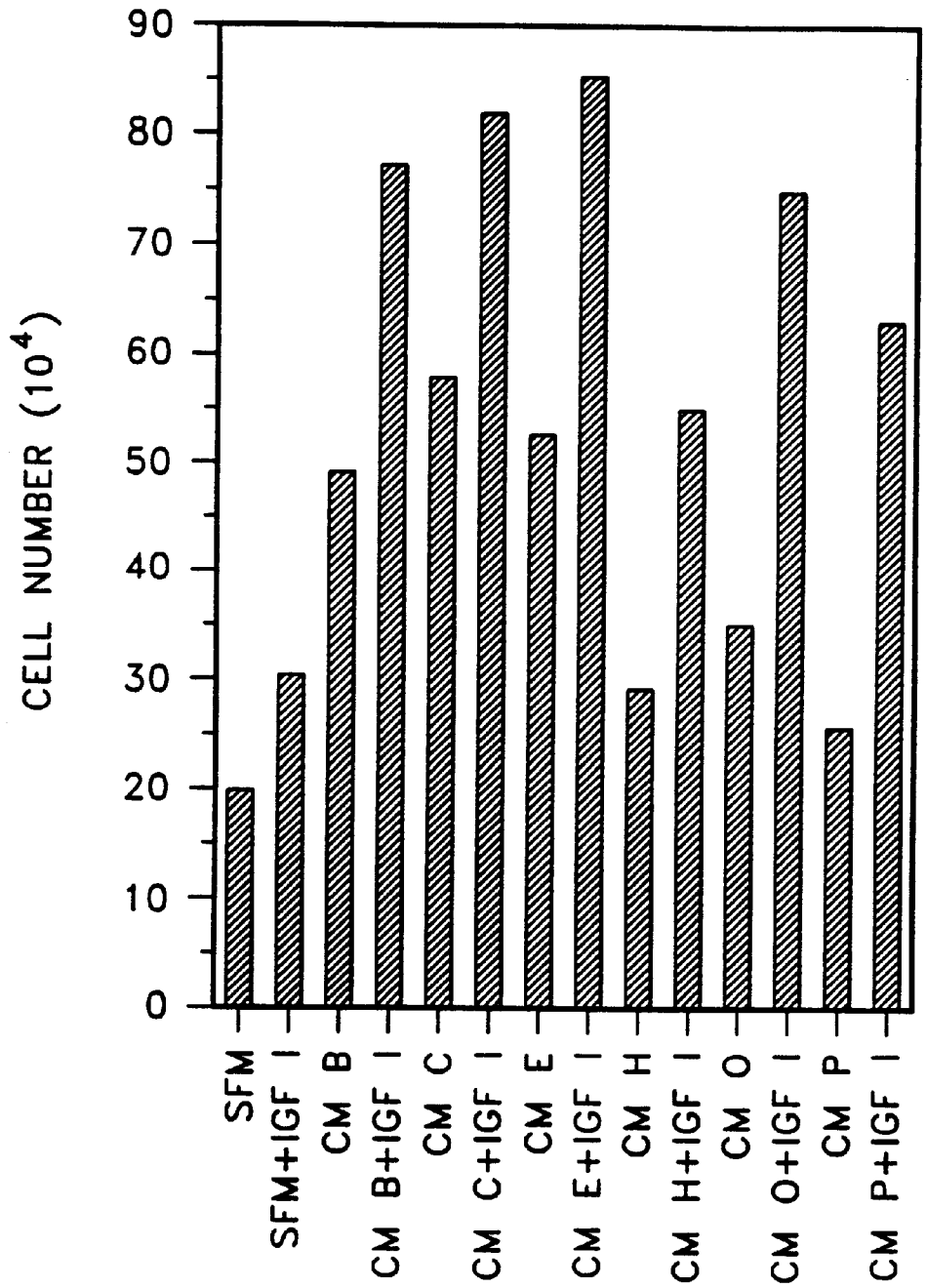
FIG. 4 shows a graph of the effect of conditioned medium from cells expressing soluble IGF-1R on the growth of p6 cells.

The effect of the medium conditioned by cells expressing soluble IGF-1R on the growth of p6 cells, which are 3T3 cells overexpressing the wild type human IGF-1R, was examined. Conditioned medium from R⁻ cells stably transfected with plasmid pIGFIRsol was collected and the growth of p6 cells determined. Conditioned medium from cell lines expressing soluble IGF-1R was prepared from pIGFIRsol-transfected cells growing at 80–90% confluence. The cells were washed with Hank's Solution and incubated in serum free medium (DMEM+0.5 mg/ml BSA+50 mg/ml transferrin) for 72 hours. Alternatively, the serum free medium can be prepared from DMEM and 2.5 mM $FeSO_4$. Conditioned medium was collected and centrifuged at 3000 rpm for five minutes to discard dead cells. FIG. 4 shows the results obtained with the conditioned medium from some of the clones. In SFM, the addition of conditioned medium has no effect on cell number, indicating that it is non toxic. However, it markedly inhibited the growth of p6 cells stimulated with IGF-1.

The conditioned medium from the same sources was then used to study its effect of colony formation in soft agar. For this purpose, T/W cells, formerly designated as (tsA)W cells (Sell, et al., *Proc. Natl. Acad. Sci. U.S.A.*, 1993, 90, 11217 and Sell, et al., *Mol. Cell. Biol.*, 1994, 14, 3604), which are 3T3-like cells expressing the SV40 large T antigen, were used. These cells form colonies in soft agar (Table 4). When conditioned medium from several clones of R⁻ cells stably transfected with plasmid pIGFIRsol, was added to the assay, it markedly inhibited colony formation, the inhibition ranging from 47 to 86 percent (Table 4).

TABLE 4

Effect of Conditioned Medium from R Cells Expressing Soluble IGF-1R on Soft Agar Growth of T/W Cells

| treatment | # of colonies in soft agar |
|---|---|
| none | 147 |
| conditioned medium from R cells | 168, 159 |
| conditioned medium from clones 1, 5, 8, 10, 14 | 38, 21, 78, 38, 56 |

T/W cells were seeded at a density of $1\times10^3$ in 10% serum, without or with the conditioned medium from R⁻ cells stably transfected with plasmid pIGFIRsol. Colonies >125 μm in diameter were scored after 3 weeks.

Conditioned medium from Balb/c 3T3 cells expressing the soluble receptor was tested for its ability to inhibit colony formation in soft agar of p6 cells, that are 3T3 cells overexpressing the wild type human IGF-1 receptor. The results are summarized in Table 5. Conditioned medium from several selected clones were tested, and they inhibited soft agar colony formation of p6 cells. The inhibition ranged from 75 to 85%.

TABLE 5

Effect of Conditioned Medium from 3T3 Cells Expressing Soluble IGF-1R on Soft Agar Growth of p6 Cells

| treatment | number of colonies in soft agar |
|---|---|
| none | 382, 350 |
| conditioned medium from Balb/c 3T3 cells | 378, 405 |
| conditioned medium from clones A, B, C, D | 84, 94, 90, 78 |
| conditioned medium from clones E, G, H, I | 57, 68, 72, 90 |
| conditioned medium from clones M, O, P | 124, 60, 59 | p6 cells were seeded at a density of $1\times10^3$ cells in 10% serum without or with the conditioned medium of several Balb/c 3T3 clones stably transfected with plasmid pIGFIRsol. Colonies were scored as in Table 4.

Example 14

Host Response

Table 6 shows that cells expressing soluble IGF-1R also induce a host response that completely protects rats from a subsequent challenge with wild type C6 rat glioblastoma cells. After the chambers (for studying apoptosis) were removed, the rats were kept for a week and were then injected subcutaneously with $10^7$ wild type rat glioblastoma cells. As usual, rats with chambers filled with wild type C6 cells were not protected from subsequent challenge with the same cells. These rats developed tumors that were palpable after 5 days, and lethal in 18–20 days. When the C6 cells incubated in the chamber were cells expressing soluble IGF-1R, all animals were completely protected from subsequent challenge with wild type C6 cells; not a single animal developed a tumor.

TABLE 6

Soluble IGF-1R Induces a Host Response in Syngeneic Rats

| cell line | percent recovery | tumor development |
|---|---|---|
| wild type | 215% | +++ |
| clone 4 | 4% | − |
| clone 6 | 8% | − |
| clone 5 | 0.1% | − |
| clone 7 | 2% | − |

What is claimed is:

1. An isolated nucleic acid molecule that comprises a nucleic acid sequence that encodes a soluble insulin-like growth factor-1 receptor peptide up to 800 amino acids comprising SEQ ID NO:4 or SEQ ID NO:5, wherein said peptide induces resistance to tumor growth.

2. A composition comprising the nucleic acid molecule of claim 1 and a pharmaceutically acceptable carrier.

3. A recombinant expression vector comprising the nucleic acid molecule of claim 1.

4. A host cell comprising the recombinant expression vector of claim 3.

5. The nucleic acid molecule of claim 1, wherein said peptide comprises SEQ ID NO:4.

6. The nucleic acid molecule of claim 1, wherein said peptide comprises SEQ ID NO:5.

7. The nucleic acid molecule of claim 1, wherein said peptide consists of SEQ ID NO:4.

8. The nucleic acid molecule of claim 1, wherein said peptide consists of SEQ ID NO:5.

9. The nucleic acid molecule of claim 1, wherein said nucleic acid molecule comprises SEQ ID NO:3.

10. An isolated nucleic acid molecule that encodes a soluble insulin-like growth factor-1 receptor comprising SEQ ID NO:4 or SEQ ID NO: 5 and terminating at amino acid 800 of SEQ ID NO:2, wherein said peptide induces resistance to tumor growth.

11. An isolated nucleic acid molecule encoding a peptide comprising SEQ ID NO: 4.

12. An isolated nucleic acid molecule encoding a peptide comprising SEQ ID NO:5.

* * * * *